(12) United States Patent
Hrabálek et al.

(10) Patent No.: US 6,187,938 B1
(45) Date of Patent: Feb. 13, 2001

(54) ω-AMINO ACID DERIVATIVES, PROCESSES OF THEIR PREPARATION AND THEIR USE

(75) Inventors: Alexandr Hrabálek, Hradec Králové ; Pavel Doležal, Hradec Krélové ; Oldřich Farsa, Bîlovice Nad Svitavou; Aleš Krebs, Chomutov; Aleš Kroutil, Kroměříž ; Martin Roman, Náchod; Zdeňka Šklubalová, Hradec Králové, all of (CZ)

(73) Assignee: Bochemie, s.r.o. (CZ)

( * ) Notice: Under 35 U.S.C. 154(b), the term of this patent shall be extended for 0 days.

(21) Appl. No.: 09/402,388

(22) PCT Filed: Apr. 1, 1998

(86) PCT No.: PCT/CZ98/00017

§ 371 Date: Dec. 21, 1999

§ 102(e) Date: Dec. 21, 1999

(87) PCT Pub. No.: WO98/45233

PCT Pub. Date: Oct. 15, 1998

(30) Foreign Application Priority Data

Apr. 4, 1997 (CZ) .................................................... 1027-97

(51) Int. Cl.[7] .................................................. C07C 101/00
(52) U.S. Cl. ............................ 554/107; 554/52; 554/106; 554/114; 560/152; 560/159; 514/554; 514/556; 514/638; 514/642
(58) Field of Search ............................. 584/52, 106, 107, 584/114; 560/152, 159; 514/554, 556, 638, 642

Primary Examiner—Deborah Carr
(74) Attorney, Agent, or Firm—Zarley, McKee, Thomte, Voorhees & Sease

(57) ABSTRACT

The invention relates to amino acid derivatives of general formula (I), wherein $R^1$ is H or $CH_3$, X is H or $NR^2R^3$, wherein $R^2$ is H, $CH_3$, COH or $COCH_3$ and $R^3$ is H, $CH_3$ or COO—Z wherein Z is $R^2R^3$ $NH^+CHR^1(CH_2)_nCOO(CH_2)_mCH_2Y$; Y is H, $CH_3$ or $NHR^4$, wherein $R^4$ a COO—$NH_3^+$ $CH_2(CH_2)_mOOC(CH_2)_nCH_3$, the meaning of group $(CH_2)_m$ being selected from alkyls, secondary alkyls, monocycloalkyls, bicycloalkyls and tricycloalkyls having from 4 to 15 carbon atoms and n having a value of from 3 to 14. ω-Amino acid derivatives of the invention are prepared by reacting a primary or secondary or monocyclic or bicyclic or tricyclic alcohol with the reaction product of an amino acid or an N-substituted amino acid with thionyl chloride, whereafter the amino group, which has been released by an amine, reacts with carbon dioxide providing a derivative of carbamic acid, or by directly reacting a primary or secondary or monocyclic or bicyclic or tricyclic alcohol with an N-substituted amino acid in the presence of a condensing agent giving the corresponding ester of the N-substituted amino acid. Thus produced compounds of formula (I) can be used as transdermal penetration enhancers. Incorporation of from 0.1 w/w percent to 5.0 w/w percent of a compound of the invention as a transdermal penetration enhancer in the vehicle of a topically applied pharmaceutical or cosmetic composition enhances transdermal penetration of pharmaceutical agents through the human or animal skin. Included further are transdermal penetration enhancers consisting of at least one compound of formula (I).

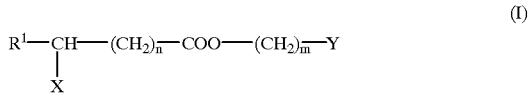

(I)

9 Claims, No Drawings

ω-AMINO ACID DERIVATIVES, PROCESSES OF THEIR PREPARATION AND THEIR USE

FIELD OF INVENTION

This invention relates to the compounds based on ω-amino acids, processes of preparation of them. The invention is also directed to application of these compounds as efficacious and safe transdermal penetration enhancers, and enhancers of transdermal penetration formed by these compounds.

BACKGROUND OF THE INVENTION

The potential advantages of transdermal administration of drugs into systemic body circulation comprise mainly principal restriction of the undesirable influence of the first pass effect based on biotransformation of agent(s) in the liver, decrease of the risk of overdosing and the risk of undesirable side effects of drug(s). Other advantages are noninvasive and continual character of administration and possibility of simple interruption of it when problematic situations arise.

During several past decades, the research effort has been oriented for using transdermal route of drug administration in the form of practically usable pharmaceutical preparations. A series of significant results has been reached in this field and has brought successes in the therapeutic and, consequently, in the commercial area. An extensive outline of this topic can be found in the review by Cleary, G. W.: Transdermal delivery systems: A medical rationale. In: Shah, V. P., Maibach, H. I.; Topical Drug Bioavailability, Bioequivalence and Penetration. Plenum Press, New York, London, 1993. pp. 16–68, and/or in the compendium by Chien, Y. W.: Novel Drug Delivery Systems. 2nd Ed., Marcel Dekker, New York, Basel, Hong Kong, 1992, 797 pp.

Transdermal penetration of drugs as such is principally limited by natural barrier properties of the skin for majority of substances. Therefore various approaches enabling transdermal absorption of agents in a reversible way are used. They include, e.g., occlusion, optimisation of polarity properties of vehicles, iontophoresis, sonophoresis, application of a concept of prodrugs and the use of transdermal absorption enhancers (accelerants or enhancers of skin penetration or permeation). The given problem is dealt in the monography by Walters, K. A., Hadgraft, J.(Eds.): Pharmaceutical Skin Penetration enhancement. Marcel Dekker, New York, Basel, Hong Kong 1993, 440 pp.

Transdermal penetration enhancers are substances, that interact with skin components or with pharmaceutical preparation components or with active agent(s) to increase the permeability of the skin for these agents in a reversible way. Enhancers of transdermal penetration extend possibilities of topical administration of agents with the purpose of systemic as well as local treatment by this route.

Information available on this topic up to 1981 was extensively dealt in the monography by Barry, B. W. Dermatological Formulations. Percuataneous Absorption. Marcel Dekker, New York, Basel, 1983, 408 pp. Newer information dealing with the given field are disposable in the article by Walters, K. A.: Penetration enhancers and their use in transdermal therapeutic systems. In: Hadgraft, J., Guy, R. H. (Eds.): Transdermal Drug Delivery. New York, Marcel Dekker, 1989, pp. 197–246 and/or in an extensive outline by Williams, A. C., Barry, B. W.: Skin absorption enhancers. CRC Crit. Rev. Ther. Drug Carrier Systems, 9 (3,4), 1992, pp. 305–353. A substantial outline comprising patent literature in the field of permeation enhancers since 1992 is given in the work by Santus, G. C., Baker, R. W.: Transdermal enhancer patent literature. J. Control. Rel., 25, 1993, pp. 1–20. Topical information dealing with the problem of skin absorption enhancers are reviewed by Kalbitz, J., Neubert, R., Wohlrab, W.: Modulation der Wirkstoffpenetration in die Haut. Pharmazie 51(9), 1996, pp. 619–637 and/or in the monography by Ranade, V. V., Hollinger, M. A.: Drug Delivery Systems. CRC Press, Boca Raton, 1995, 364 pp.

The use of permeation enhancers or their combinations for transdermal administration of various drug(s) is described in numerous recent patents, such as PCT Int. Appl. WO 9402, 119; PCT Int. Appi. WO 9323,019; PCT Int. Appl.WO 9323,025; Eur. Pat. Appl. EP 569, 338; PCT Int. Appl. 9325, 197; Eur. Pat. Appl. EP 581,587; Eur. Pat. Appl. EP 582,458; Eur. Pat. Appl. EP 680,759; Eur. Pat. Appl. 644,922; PCT Int. Appl. WO 9303,697; PCT Int. Appl. WO 9603,131; PCT Int. Appl. WO 9706,788.

There is a large number of substances interacting with the skin and its *stratum corneum*. Transdermal penetration enhancers as substances used in pharmaceutical preparations have to meet a set of qualitative criteria; they must not be toxic, they must not irritate, allergize or sensitize the skin and they should be pharmacologically inert at the concentrations required to exert adequate permeation action. Their effect shoud be immediate, predictive and reversible. At the same time they should be easily incorporated into pharmaceutical preparations as well as cosmetically acceptable (addapted from: Barry, B. W.: Dermatological Formulations. Percutaneous Absorption. Marcel Dekker, New York, Basel, 1983, pp. 167–172; Hadgraft, J.: Penetration enhancers in percutaneous absorption. Pharm. Int., 5, 1984, pp. 252–4; Pfister, W. R., Hsieh, D. S. T.: Permeation enhancers compatible with transdermal drug delivery systems. Part I., II. Pharm. Technol. Int., 3 (1) 1991, pp. 32–6, 3 (2), pp.28–32.

It is understandable that no univeral permeation enhancer has not been and probably would not be identified.

Derivatives of ω-amino acids, both cyclic and linear, can be included, however, among very promising and recently intensively studied substances exerting enhancing effect on transdermal penetration and permeation. The most significant substance of this group is 1-dodecylazacycloheptan-2-one (laurocapram, Azone®), patented in 1976 (Rajadhyaksha, V. J., Vieo, M.: U.S. Pat. No. 3,989,815 and U.S. Pat. No. 3,989,916). Some other substances being used for this purpose are aryl-methyl-2-pyrrolidone (U.S. Pat. No. 3,969,516) and, for instance, derivatives of azepanone substituted in various ways (Santus, G. C., Baker, R. W.: J. Control. Release 25, 1993, pp. 1–20). Their disadvantage is that they cannot be easily dispersed in aqueous solutions and their effect is inhibited by the presence of some auxiliary substances commonly used as constituents in topical preparations. For instance, auxiliary substances of the paraffinic carbohydrate type (e.g., petrolatum) can completely inhibit permeation enhancing effect of laurocapram (Stoughton, R. B., McClure, W. O.: Azone®: A new non-toxic enhancer of cutaneous penetration. Drug. Dev. Ind. Pharm. 9, 1983, pp. 725–744). Within the group of linear derivatives of ω-amino acids, esters of lysine (Eur. Pat. Appl. No. 84200822) and/or esters of ε-aminocaproic acid (CZ Pat. 276300) can be mentioned.

As used herein, the term "transdermal penetration enhancer" refers to the substance(s) applicable in pharmaceutical preparations to increase penetration and permeation of drug(s) topically administered on human or animal skin with the aim of reaching therapeutically effective concentrations of drug(s) and other pharmacologically active agent (s) in deeper layers of the skin and/or adjacent tissues or for reaching effective concentrations of active agent(s) in systemic circulation of a living organism.

DETAILED DESCRIPTION OF THE INVENTION

The invention is directed to carbamic acid salts of the general formula (I)

$$X—CH_2—(CH_2)_n—COO—A—Y \quad (I)$$

wherein
either X is hydrogen and Y is a group of formula $NHCOO^-H_3N^+—A—OCO—(CH_2)_{n-1}—CH_3$, or X is a group of formula $NHCOO^-H_3N^+(CH_2)_{n+1}—COO—A—H$ and Y is hydrogen, and wherein A is a $C_5–C_{16}$ alkylene or a $C_5–C_{12}$ cycloalkanediyl, benzocycloalkanediyl, bicycloalkanediyl or tricycloalkanediyl and n is an integer from 3 to 14.

The invention also relates to a method for the preparation of carbamic acid salts of the general formula (I) wherein an amino acid hydrochloride of general formula $$Cl^-H_3N^+—(CH_2)_{n+1}—COOH$$

wherein n is as defined above, is reacted with thionyl chloride at a temperature of from 10° C. to 40° C. and the resulting aminoacylchloride hydrochloride is reacted with at least an equimolar amount of an alcohol selected from the group including primary monocyclic, bicyclic and tricyclic alcohols of general formula $$A—OH$$

wherein A is defined as above, in an aprotic medium at a temperature of from 20° C. to 90° C., giving rise to an amino acid ester hydrochloride which is then reacted with an amine in an aqueous or anhydrous medium, the basic ester being thereafter reacted with carbon dioxide.

The invention also relates to a method for the preparation of carbamic acid salts of the general formula (I) characterised in that a carboxylic acid chloride of general formula $$CH_3—(CH_2)_n—COCl$$

wherein n is as defined above, is reacted with an α,ω-amino alcohol hydrochloride of general formula $$HO—A—NH_3^+Cl^-$$

wherein A is as defined above, at a temperature of from 20° C. to 90° C. in an aprotic medium the amino ester hydrochloride being thereafter reacted with an amine in an aqueous or anhydrous medium and the basic amino ester being allowed to react with carbon dioxide.

The invention also relates to the use of the compounds of the general formula (I) as transdermal penetration enhancers in topical pharmaceutical and cosmetic preparations. In more detail the invention relates to the use of these compounds as enhancers of transdermal penetration from the hydrophobic vehicle of a topical preparation in the amount from 0.1 to 5 w/w per cent, preferably from 0.5 to 2.5 w/w per cent or from a hydrophilic medium of a topical preparation in the amount from 0.1 to 5 w/w per cent, preferably from 0.5 to 1 w/w per cent.

Finally, the invention also relates to the transdermal penetration enhancers destined for enhancing the penetration of physiologically active substances applied topically to human or animal skin in order to produce therapeutically effective concentrations of the active substances in deeper layers of the skin or produce therapeutically effective concentrations of the active substances in the circulatory system of living organisms, consisting of at least one compound of the general formula (I).

The processes of preparation of compounds based on general formula (I) are described for selected substances in the Examples. These examples illustrate preparation of various types of new substances which are the subject of the invention. Substances synthesised by inventors are characterised in the pertinent Tables within the paragraph Examples.

The compounds of the general formula (I) are stable substances under the normal conditions. They can be easily prepared by simple laboratory procedures in small amounts as well as produced in large scale with high purity and large yield, which belongs among their advantages. Compounds based on ω-amino acids having the structure of general formula (I) are therefore relatively cheap.

Until now tested compounds of the general formula (I) have a very low oral toxicity and relatively low toxicity at intraperitoneous administration. For instance, when orally administered 8 g/kg of dodecyloxycarbonylpentylammonium dodecyloxycarbonylpentyl-carbamate (product No. 1.7) to a group of mice no mortality or significant changes in behaviour were observed. The value of $LD_{50}$ of this substance after intraperitoneal administration was about 160 mg/kg of the weight of laboratory mice. In comparative tests of embryotoxicity carried out by the CHEST I method on chicken embryos it has been proved, for instance, that embryotoxic potential of the above mentioned compound according to the invention is one order lower comparing to N-decyl-2-pyrrolidone and identical with 1-dodecylazacycloheptan-2-one (Azone®), that are as substances frequently used for transdermal penetration enhancement. Results of comparative experiments in which some other known agents were tested under the same conditions proved that embryotoxicity of above mentioned product No. 1.7 corresponds, for instance, to that of ketoprofen and ibuprofen. The compounds according to the invention tested so far are non-irritative when administered to skin and comply to the requirements of a pertinent paragraph of the Czechoslovak Pharmacopoeia 4, ed. 1987, (ČSL 4).

The advantage of practical use of compounds as enhancers according to the invention is that they are technologically easily incorporable with the majority of liquid or semi-solid vehicles commonly used in topical pharmaceutical or cosmetic preparation. These can be hydrophobic vehicles from the group of vegetable oils (e.g., sunflower oil, olive oil), synthetic liquid waxes (e.g., isopropyl myristate, isopropyl palmitate) or liquid paraffin, petrolatum, etc., or their mixtures as well as common hydrophillic vehicles (e.g., water, propylene glycol, glycerol, low molecular polyethylene glycoles) or their mixtures.

The advantage of using these compounds according to the invention as enhancers is that they are effective at relatively low concentrations in the range from 0.1 per cent to 5 per cent, preferably between 0.3 per cent to 2.5 per cent in relation to the total weight of the topical preparation.

It is known that many of permeation enhancers are effective with one drug but ineffective with other drug. That is why the inventors carried out in vitro permeation experiments to evaluate enhancing activity of chosen substances of the general formula (I). Among active agents belonging to therapeutically completely different groups that showed significant increase of skin penetration when using compounds according to the invention as enhancers of transdermal penetration, are polar drug (e.g., 5-fluorouracil), agents of medium polarity (e.g., aciclovir, flobufen, theophylline) as well as non-polar substance generally very hardly dissolving (e.g., griseofulvin).

Effectiveness of compounds according to the invention to enhance transdermal permeation was evaluated in in vitro finite dose, or flow out experiments on excised human skin, or *stratum corneum,* respectively, carried out under the conditions described in more details in paper by Doležal P., Hrabálek, A., Semecký, V.: ε-Amino-caproic acid esters as transdermal penetration enhancing agents. Pharm. Res. 10, 1993, pp.1015–1019, or Akhter, S. A., et al.: An automated diffusion apparatus for studying skin penetration. Int. J. Pharm., 21, 1984, pp. 17–26, respectively.

To express enhancing efficiency of compounds according to the invention, mean values of enhancement ratio, ER's, as the ratios of the permeant flux ($\mu g/cm^2 \cdot h^{-1}$) obtained by help donor samples containing enhancer tested comparing to the value of permeant flux for pertinent control samples (i.e. donor without the content of enhancer tested) were used.

For instance, some of the chosen results obtained by evaluation of the enhancement efficiancy with the use of product No. 1.7 are as follows:

ER=43.6±11.5 for theophylliine from aquaeous donor medium saturated with theophylline and with the content of 1 per cent of enhancer;

ER=16.8±5.8 for theophylline from the olive oil vehicle saturated by theophylline with the content of 1 per cent of enhancer;

ER=4.2±1.6 for flobufen from the medium of hydrophobic cream with the content of 5 per cent of flobufen and 2.5 per cent of enhancer;

EP=24.7±8.2 for griseofulvin from the mixture of propylene glycol and water (2:3) with the content of 0.1 per cent of griesofulvin and 2 per cent of enhancer;

EP=7.8±3.1 for aciclovir from propylene glycole with the content of 1 per cent of aciclovir and 1 per cent of enhancer;

EP=88.0±37 for 5-fluorouracil from aquaeous medium saurated by 5-fluorouracil with the content of 0.3 per cent of enhancer.

Within a set of screening in vitro experiments oriented to evaluation of transdermal enhancing efficiency of substances of general formula (1) that were synthetized by inventors. Theophylline was used as a model permeant.

EXAMPLES

Example 1

Hexyloxycarbonylpentylammomium hexyloxycarbonylpentylcarbamate 6-aminohexanoic acid hydrochloride (0.1 mol) was treated with thionyl chloride (0.2 mol) at 35° C. until the mixture became homogeneous. The excess thionyl chloride was then removed under reduced pressure, a solution of hexanol (0.1 mol) in dry $CHCl_3$ (100 ml) was added to the residue, and the resultant mixture was heated at reflux. After 1 hour at reflux, chloroform was evaporated under reduced pressure, the residue was dried, and by-product hydrogen chloride removed. The crude compound was dissolved in water, triethyl amine (0.15 mol) was added to the solution, and the resultant mixture was extracted with diethyl ether. The ethereal phase was dried over anhydrous $Na_2SO_4$, solvent evaporated, and the crude product was allowed to stir in a $CO_2$ atmosphere for 1 hour. Traces of triethyl amine were removed upon standing over a vessel containing sulfuric acid under vacuum, and the product crystallised from toluene.

Example 3

Cyclododecyloxycarbonylpentylammonium cyclododecyloxycarbonylpentylcarbamate 6-aminohexanoic acid hydrochloride (0.1 mol) was treated with thionyl chloride (0.2 mol) at 40° C. until the mixture became homogeneous. The excess thionyl chloride was then removed under reduced pressure, a solution of cyclododecanol (0.1 mol) in dry dimethyl formamide (100 ml) was added to the residue, and the resultant mixture was heated at 90%. After 1 hour at this temperature, the solvent was evaporated under reduced pressure, the residue was dried, and by-product hydrogen chloride removed. The crude compound was dissolved in water, triethyl amine (0.15 mol) was added to the solution, and the resultant mixture was extracted with diethyl ether. The ethereal phase was dried over anhydrous $Na_2SO_4$, solvent evaporated, and the crude product was allowed to stir in a $CO_2$ atmosphere for 1 hour. Traces of triethyl amine were removed upon standing over a vessel containing sulfuric acid under vacuum, and the product crystallised from toluene.

Example 6

Hexadecanoyloxyhexylammonium hexadecanoyloxyhexylcarbamate

Hexadecanoic acid (0.01 mol) was treated with thionyl chloride (0.15 mol) in dry toluene (100 ml) at reflux. After 1 hour at reflux, the solvent and the excess reagent were removed under reduced pressure, a suspension of 1,6-aminohexanol hydrochloride (0.01 mol) in dry chloroform was added to the residue, and the reaction mixture was heated at 64° C. until it became homogeneous. After cooling to ambient temperature, the solution was concentrated, the aminoester hydrochloride was crystallised from ethanol/diethyl ether mixture, and subjected to reaction with with triethyl amine in an aqueous solution. Following the separation/drying/solvent removal cycle, the crude product was allowed to stir in a $CO_2$ atmosphere for 1 hour. Traces of triethyl amine were removed upon standing over a vessel containing sulfuric acid under vacuum, and the product crystallised from toluene.

TABLE I

Carbamic acid salts based on the primary alkyl aminoalkanoates

| Starting ω-aminoacid | Starting alcohol | Product No. | Product |
| --- | --- | --- | --- |
| 6-Aminohexanoic acid | 1-Hexanol | 1.1 | Hexyloxycarbonylpentylammonium hexyloxycarbonylpentylcarbamate |
| | 1-Heptanol | 1.2 | Heptyloxycarbonylpentylammonium heptyloxycarbonylpentylcarbamate |
| | 1-Octanol | 1.3 | Octyloxycarbonylpentylammonium octyloxycarbonylpentylcarbamate |
| | 1-Nonanol | 1.4 | Nonyloxycarbonylpentylammonium nonyloxycarbonylpentylcarbamate |
| | 1-Decanol | 1.5 | Decyloxycarbonylpentylammonium decyloxycarbonylpentylcarbamate |
| | 1-Undecanol | 1.6 | Undecyloxycarbonylpentylammonium undecyloxycarbonylpentylcarbamate |
| | 1-Dodecanol | 1.7 | Dodecyloxycarbonylpentylammonium dodecyloxycarbonylpentylcarbamate |
| | 1-Tetradecanol | 1.8 | Tetradecyloxycarbonylpentylammonium tetradecyloxycarbonylpentylcarbamate |

TABLE I-continued

Carbamic acid salts based on the primary alkyl aminoalkanoates

| Starting ω-aminoacid | Starting alcohol | Product No. | Product |
|---|---|---|---|
| | 1-Hexadecanol | 1.9 | Hexadecyloxycarbonylpentylammonium hexadecyloxycarbonylpentylcarbamate |
| 7-Aminoheptanoic acid | 1-Pentanol | 1.10 | Pentyloxycarbonylhexylammonium pentyloxycarbonylhexylcarbamate |
| | 1-Hexanol | 1.11 | Hexyloxycarbonylhexylammonium hexyloxycarbonylhexylcarbamate |
| | 1-Heptanol | 1.12 | Heptyloxycarbonylhexylammonium heptyloxycarbonylhexylcarbamate |
| | 1-Octanol | 1.13 | Octyloxycarbonylhexylammonium octyloxycarbonylhexylcarbamate |
| | 1-Nonanol | 1.14 | Nonyloxycarbonylhexylammonium nonyloxycarbonylhexylcarbamate |
| | 1-Decanol | 1.15 | Decyloxycarbonylhexylammonium decyloxycarbonylhexylcarbamate |
| | 1-Undecanol | 1.16 | Undecyloxycarbonylhexylammonium undecyloxycarbonylhexylcarbamate |
| | 1-Dodecanol | 1.17 | Dodecyloxycarbonylhexylammonium dodecyloxycarbonylhexylcarbamate |
| | 1-Tetradecanol | 1.18 | Tetradecyloxycarbonylhexylammonium tetradecyloxycarbonylhexylcarbamate |
| | 1-Hexadecanol | 1.19 | Hexadecyloxycarbonylhexylammonium hexadecyloxycarbonylhexylcarbamate |
| 8-Aminooctanoic acid | 1-Pentanol | 1.20 | Pentyloxycarbonylheptylammonium pentyloxycarbonylheptylcarbamate |
| | 1-Hexanol | 1.21 | Hexyloxycarbonylhexylammonium hexyloxycarbonylhexylcarbamate |
| | 1-Heptanol | 1.22 | Heptyloxycarbonylhexylammonium heptyloxycarbonylhexylcarbamate |
| | 1-Octanol | 1.23 | Octyloxycarbonylhexylammonium octyloxycarbonylhexylcarbamate |
| | 1-Nonanol | 1.24 | Nonyloxycarbonylhexylammonium nonyloxycarbonylhexylcarbamate |
| | 1-Decanol | 1.25 | Decyloxycarbonylhexylammonium decyloxycarbonylhexylcarbamate |
| | 1-Undecanol | 1.26 | Undecyloxycarbonylhexylammonium undecyloxycarbonylhexylcarbamate |
| | 1-Dodecanol | 1.27 | Dodecyloxycarbonylhexylammonium dodecyloxycarbonylhexylcarbamate |
| | 1-Tetradecanol | 1.28 | Tetradecyloxycarbonylhexylammonium tetradecyloxycarbonylhexylcarbamate |
| | 1-Hexadecanol | 1.29 | Hexadecyloxycarbonylhexylammonium hexadecyloxycarbonylhexylcarbamate |
| 6-Methylaminohexanoic acid | 1-Undecanol | 1.30 | Undecyloxycarbonylpentylmethylammonium undecyloxycarbonylpentylmethylcarbamate |
| | 1-Dodecanol | 1.31 | Dodecyloxycarbonylpentylmethylammonium dodecyloxycarbonylpentylmethylcarbamate |

On the basis of the method according to Example 2 thirty nine of new substances were synthetised where 6-aminohexanoic acid hydrochloride (within the first group), 7-aminoheptanoic acid hydrochloride (within the second group), and, 8-aminooctanoic acid hydrochloride (within the third group) as starting substances were used. These 39 substances are presented in Table II. The physicochemical characteristics of these substances are summarised in Table X and Table XVII, respectively, and selected efficiency data are presented in Table XXVI.

TABLE II

Secondary alkyl-ω-aminoalkanoates

| Starting ω-amino acid | Starting alcohol | Product No. | Product No. |
|---|---|---|---|
| 6-amino-hexanoic acid | 2-Heptanol | 2.1 | 2-Heptyl 6-aminohexanoate |
| | 3-Heptanol | 2.2 | 3-Heptyl 6-aminohexanoate |
| | 4-Heptanol | 2.3 | 4-Heptyl 6-aminohexanoate |
| | 2-Octanol | 2.4 | 2-Octyl 6-aminohexanoate |
| | 3-Octanol | 2.5 | 3-Octyl 6-aminohexanoate |
| | 2-Nonanol | 2.6 | 2-Nonyl 6-aminohexanoate |
| | 3-Nonanol | 2.7 | 3-Nonyl 6-aminohexanoate |
| | 4-Nonanol | 2.8 | 4-Nonyl 6-aminohexanoate |
| | 5-Nonanol | 2.9 | 5-Nonyl 6-aminohexanoate |
| | 2-Decanol | 2.10 | 2-Decyl 6-aminohexanoate |
| | 2-Undecanol | 2.11 | 2-Undecyl 6-aminohexanoate |
| | 2-Dodecanol | 2.12 | 2-Dodecyl 6-aminohexanoate |
| | 7-Tetradecanol | 2.13 | 7-Tetradecyl 6-aminohexanoate |
| 7-amino-heptanoic acid | 2-Heptanol | 2.14 | 2-Heptyl 7-aminoheptanoate |
| | 3-Heptanol | 2.15 | 3-Heptyl 7-aminoheptanoate |
| | 4-Heptanol | 2.16 | 4-Heptyl 7-aminoheptanoate |
| | 2-Octanol | 2.17 | 2-Octyl 7-aminoheptanoate |
| | 3-Octanol | 2.18 | 3-Octyl 7-aminoheptanoate |
| | 2-Nonanol | 2.19 | 2-Nonyl 7-aminoheptanoate |
| | 3-Nonanol | 2.20 | 3-Nonyl 7-aminoheptanoate |
| | 4-Nonanol | 2.21 | 4-Nonyl 7-aminoheptanoate |
| | 5-Nonanol | 2.22 | 5-Nonyl 7-aminoheptanoate |
| | 2-Decanol | 2.23 | 2-Decyl 7-aminoheptanoate |
| | 2-Undecanol | 2.24 | 2-Undecyl 7-aminoheptanoate |
| | 2-Dodecanol | 2.25 | 2-Dodecyl 7-aminoheptanoate |
| | 7-Tetradecanol | 2.26 | 7-Tetradecyl 7-aminoheptanoate |

TABLE II-continued

Secondary alkyl-ω-aminoalkanoates

| Starting ω-amino acid | Starting alcohol | Product No. | Product No. |
|---|---|---|---|
| 8-amino-octanoic acid | 2-Heptanol | 2.27 | 2-Heptyl 8-aminooctanoate |
| | 3-Heptanol | 2.28 | 3-Heptyl 8-aminooctanoate |
| | 4-Heptanol | 2.29 | 4-Heptyl 8-aminooctanoate |
| | 2-Octanol | 2.30 | 2-Octyl 8-aminooctanoate |
| | 3-Octanol | 2.31 | 3-Octyl 8-aminooctanoate |
| | 2-Nonanol | 2.32 | 2-Nonyl 8-aminooctanoate |
| | 3-Nonanol | 2.33 | 3-Nonyl 8-aminooctanoate |
| | 4-Nonanol | 2.34 | 4-Nonyl 8-aminooctanoate |
| | 5-Nonanol | 2.35 | 5-Nonyl 8-aminooctanoate |
| | 2-Decanol | 2.36 | 2-Decyl 8-aminooctanoate |
| | 2-Undecanol | 2.37 | 2-Undecyl 8-aminooctanoate |
| | 2-Dodecanol | 2.38 | 2-Dodecyl 8-aminooctanoate |
| | 7-Tetradecanol | 2.39 | 7-Tetradecyl 8-aminooctanoate |

On the basis of the method according to Example 2 eight of new substances were synthetised where 6-methylaminohexanoic acid hydrochloride (within the first group), and, 8-aminooctanoic acid hydrochloride (within the second group) as starting substances were used. These 8 substances are presented in Table III. The physicochemical characteristics of these substances are summarised in Table XI and Table XVIII, respectively, and selected efficiency data are presented in Table XXVI.

TABLE III

Primary alkyl 6-methyl- and 6-dimethylaminohexanoates

| Starting ω-amino acid | Starting alcohol | Product No. | Product No. |
|---|---|---|---|
| 6-Methyl-amino- | 1-Octanol | 3.1 | Octyl 6-methylaminohexanoate |
| | 1-Nonanol | 3.2 | Nonyl 6-methylaminohexanoate |

TABLE III-continued

Primary alkyl 6-methyl- and 6-dimethylaminohexanoates

| Starting ω-amino acid | Starting alcohol | Product No. | Product No. |
|---|---|---|---|
| hexanoic acid | 1-Decanol | 3.3 | Decyl 6-methylaminohexanoate |
| 6-Dimeth-ylamino-hexanoic acid | 1-Octanol | 3.4 | Octyl 6-dimethylaminohexanoate |
| | 1-Nonanol | 3.5 | Nonyl 6-dimethylaminohexanoate |
| | 1-Decanol | 3.6 | Decyl 6-dimethylaminohexanoate |
| | 1-Undecanol | 3.7 | Undecyl 6-dimethylaminohexanoate |
| | 1-Dodecanol | 3.8 | Dodecyl 6-dimethylaminohexanoate |

On the basis of the method according to Example 2 nine of new substances were synthetised where 6-aminohexanoic acid hydrochloride (within the first group), 7-aminoheptanoic acid hydrochloride (within the second group), and, 8-aminooctanoic acid hydrochloride (within the third group) as starting substances were used. These 9 substances are presented in Table IV. The physicochemical characteristics of these substances are summarised in TABLE XIII and TABLE XXIII, respectively, and selected efficiency data are presented in TABLE XXVI.

TABLE V-continued

Cycloalkyl ω-aminoalkanoates

| Starting ω-amino acid | Starting alcohol | Product No. | Product |
|---|---|---|---|
| octanoic acid | Cyclooctanol | 5.9 | Cyclooctyl 8-amino octanoate |

On the basis of the method according to Example 4 twenty three of new substances were synthetised where 5-acetylaminopentanoic acid (within the first group), 6-acetylaminohexanoic acid (within the second group), 7-acetylaminoheptanoic acid and (within the third group), and 8-aminooctanoic acid hydrochloride (within the fourth group) as starting substances were used. These 23 substances are presented in Table VI. The physicochemical characteristics of these substances are summarised in Table XV, Table XX, and Table XXIV respectively, and selected efficiency data are presented in Table XXVI.

TABLE IV

Carbamic acid salts based on the cyclic ω-aminoalkanoates

| Starting ω-aminoacid | Starting alcohol | Product No. | Product |
|---|---|---|---|
| 6-Aminohexanoic acid | Cyclododecanol | 4.1 | Cyclododecyloxycarbonylpentylammonium cyclododecyloxycarbonylpentylcarbamate |
| | 2-Indanol | 4.2 | 2-Indanyloxycarbonylpentylammonium 2-indanyloxycarbonylpentylcarbamate |
| | 1-Adamantanol | 4.3 | 1-Adamantyloxycarbonylpentylammonium 1-adamantyloxycarbonylpentylcarbamate |
| 7-Aminoheptanoic acid | Cyclododecanol | 4.4 | Cyclododecyloxycarbonylhexylammonium cyclododecyloxycarbonylhexylcarbamate |
| | 2-Indanol | 4.5 | 2-Indanyloxycarbonylhexylammonium 2-indanyloxycarbonylhexylcarbamate |
| | 1-Adamantanol | 4.6 | 1-Adamantyloxycarbonylhexylammonium 1-adamantyloxycarbonylhexylcarbamate |
| 8-Aminooctanoic acid | Cyclododecanol | 4.7 | Cyclododecyloxycarbonylheptylammonium cyclododecyloxycarbonylheptylcarbamate |
| | 2-Indanol | 4.8 | 2-Indanyloxycarbon-heptylammonium 2-indanyloxycarbonylheptylcarbamate |
| | 1-Adamantanol | 4.9 | 1-Adamantyloxycarbonylheptylammonium 1-adamantyloxycarbonylheptylcarbamate |

On the basis of the method according to Example 2 nine of new substances were synthetised where 6-aminohexanoic acid hydrochloride (within the first group), 7-aminoheptanoic acid hydrochloride (within the second group), and, 8-aminooctanoic acid hydrochloride (within the third group) as starting substances were used. These 9 substances are presented in Table V. The physicochemical characteristics of these substances are summarised in Table XII and Table XVIX, respectively, and selected efficiency data are presented in Table XXVI.

TABLE V

Cycloalkyl ω-aminoalkanoates

| Starting ω-amino acid | Starting alcohol | Product No. | Product |
|---|---|---|---|
| 6-Amino-hexanoic acid | Cyclopentanol | 5.1 | Cyclopentyl 6-amino hexanoate |
| | Cyclohexanol | 5.2 | Cyclohexyl 6-amino hexanoate |
| | Cycloheptanol | 5.3 | Cycloheptyl 6-amino hexanoate |
| | Cyclooctanol | 5.4 | Cyclooctyl 6-amino hexanoate |
| 7-Amino-heptanoic acid | Cyclohexanol | 5.5 | Cyclohexyl 7-amino heptanoate |
| | Cycloheptanol | 5.6 | Cycloheptyl 7-amino heptanoate |
| | Cyclooctanol | 5.7 | Cyclooctyl 7-amino heptanoate |
| 8-Amino- | Cycloheptanol | 5.8 | Cycloheptyl 8-amino octanoate |

TABLE VI

Primary alkyl ω-acetylaminoalkanoates

| Starting ω-acetyl-amino acid | Starting alcohol | Product No. | Product |
|---|---|---|---|
| 5-Acetyl-amino-pentanoic acid | 1-Octanol | 6.1 | Octyl 5-acetylaminopentanoate |
| | 1-Nonanol | 6.2 | Nonyl 5-acetylaminopentanoate |
| | 1-Decanol | 6.3 | Decyl 5-acetylaminopentanoate |
| | 1-Undecanol | 6.4 | Undecyl 5-acetylaminopentanoate |
| | 1-Dodecanol | 6.5 | Dodecyl 5-acetylaminopentanoate |
| 6-Acetyl-amino-hexanoic acid | 1-Hexanol | 6.6 | Hexyl 6-acetylaminohexanoate |
| | 1-Heptanol | 6.7 | Heptyl 6-acetylaminohexanoate |
| | 1-Octanol | 6.8 | Octyl 6-acetylaminohexanoate |
| | 1-Nonanol | 6.9 | Nonyl 6-acetylaminohexanoate |
| | 1-Decanol | 6.10 | Decyl 6-acetylaminohexanoate |
| | 1-Undecanol | 6.11 | Undecyl 6-acetylaminohexanoate |
| | 1-Dodecanol | 6.12 | Dodecyl 6-acetylaminohexanoate |
| 7-Acetyl-amino-heptanoic acid | 1-Pentanol | 6.13 | Pentyl 7-acetylaminohexanoate |
| | 1-Heptanol | 6.14 | Heptyl 7-acetylaminohexanoate |
| | 1-Octanol | 6.15 | Octyl 7-acetylaminohexanoate |
| | 1-Nonanol | 6.16 | Nonyl 7-acetylaminohexanoate |
| | 1-Decanol | 6.17 | Decyl 7-acetylaminohexanoate |
| | 1-Undecanol | 6.18 | Undecyl 7-acetylaminohexanoate |
| | 1-Dodecanol | 6.19 | Dodecyl 7-acetylaminohexanoate |
| 8-Acetyl- | 1-Pentanol | 6.20 | Pentyl 8-acetylaminooctanoate |

TABLE VI-continued

Primary alkyl ω-acetylaminoalkanoates

| Starting ω-acetyl-amino acid | Starting alcohol | Product No. | Product |
|---|---|---|---|
| amino-octanoic acid | 1-Octanol | 6.21 | Octyl 8-acetylaminooctanoate |
| | 1-Decanol | 6.22 | Decyl 8-acetylaminooctanoate |
| | 1-Dodecanol | 6.23 | Dodecyl 8-acetylaminooctanoate |

On the basis of the method according to Example 5 thirty seven of new substances were synthetised where 5-acetylamiopentanoic acid (within the first group), 6-acetylaminohexanoic acid (within the second group), 7-acetylaminoheptanoic acid and (within the third group), and 8-aminooctanoic acid hydrochloride (within the fourth group) as starting substances were used. These 37 substances are presented in Table VII. The physicochemical characteristics of these substances are summarised in Table XVI, Table XXI, respectively, and selected efficiency data are presented in Table XXVI.

TABLE VII

Secondary alkyl ω-acetaminoalkanoates

| Starting ω-acetyl-amino acid | Starting alcohol | Product No. | Product |
|---|---|---|---|
| 5-Ace-tyl-amino-penta-noic acid | 2-Heptanol | 7.1 | 2-Heptyl 5-acetylaminopentanoate |
| | 3-Heptanol | 7.2 | 3-Heptyl 5-acetylaminopentanoate |
| | 2-Octanol | 7.3 | 2-Octyl 5-acetylaminopentanoate |
| | 2-Nonanol | 7.4 | 2-Nonyl 5-acetylaminopentanoate |
| | 3-Nonanol | 7.5 | 3-Nonyl 5-acetylaminopentanoate |
| | 2-Decanol | 7.6 | 2-Decyl 5-acetylaminopentanoate |
| 6-Ace-tyl-amino-hexa-noic acid | 2-Heptanol | 7.7 | 2-Heptyl 6-acetylaminohexanoate |
| | 4-Heptanol | 7.8 | 4-Heptyl 6-acetylaminohexanoate |
| | 2-Octanol | 7.9 | 2-Octyl 6-acetylaminohexanoate |
| | 3-Octanol | 7.10 | 3-Octyl 6-acetylaminohexanoate |
| | 4-Nonanol | 7.11 | 4-Nonyl 6-acetylaminohexanoate |
| | 5-Nonanol | 7.12 | 5-Nonyl 6-acetylaminohexanoate |

TABLE VII-continued

Secondary alkyl ω-acetaminoalkanoates

| Starting ω-acetyl-amino acid | Starting alcohol | Product No. | Product |
|---|---|---|---|
| | 2-Decanol | 7.13 | 2-Decyl 6-acetylaminohexanoate |
| | 2-Undecanol | 7.14 | 2-Undecyl 6-acetylaminohexanoate |
| | 7-Tetradecanol | 7.15 | 7-Tetradecyl 6-acetylaminohexanoate |
| 7-Ace-tyl-amino-hepta-noic acid | 2-Heptanol | 7.16 | 2-Heptyl 7-acetylaminoheptanoate |
| | 3-Heptanol | 7.17 | 3-Heptyl 7-acetylaminoheptanoate |
| | 4-Heptanol | 7.18 | 4-Heptyl 7-acetylaminoheptanoate |
| | 2-Octanol | 7.19 | 2-Octyl 7-acetylaminoheptanoate |
| | 3-Octanol | 7.20 | 3-Octyl 7-acetylaminoheptanoate |
| | 2-Nonanol | 7.21 | 2-Nonyl 7-acetylaminoheptanoate |
| | 3-Nonanol | 7.22 | 3-Nonyl 7-acetylaminoheptanoate |
| | 4-Nonanol | 7.23 | 4-Nonyl 7-acetylaminoheptanoate |
| | 5-Nonanol | 7.24 | 5-Nonyl 7-acetylaminoheptanoate |
| | 2-Decanol | 7.25 | 2-Decyl 7-acetylaminoheptanoate |
| | 2-Undecanol | 7.26 | 2-Undecyl 7-acetylaminoheptanoate |
| 8-Ace-tyl-amino-octa-noic acid | 2-Heptanol | 7.27 | 2-Heptyl 8-aminoacetyloctanoate |
| | 3-Heptanol | 7.28 | 3-Heptyl 8-aminoacetyloctanoate |
| | 4-Heptanol | 7.29 | 4-Heptyl 8-aminoacetyloctanoate |
| | 2-Octanol | 7.30 | 2-Octyl 8-aminoacetyloctanoate |
| | 3-Octanol | 7.31 | 3-Octyl 8-aminoacetyloctanoate |
| | 2-Nonanol | 7.32 | 2-Nonyl 8-aminoacetyloctanoate |
| | 3-Nonanol | 7.33 | 3-Nonyl 8-aminoacetyloctanoate |
| | 4-Nonanol | 7.34 | 4-Nonyl 8-aminoacetyloctanoate |
| | 5-Nonanol | 7.35 | 5-Nonyl 8-aminoacetyloctanoate |
| | 2-Decanol | 7.36 | 2-Decyl 8-aminoacetyloctanoate |
| | 2-Undecanol | 7.37 | 2-Undecyl 8-aminoacetyloctanoate |

On the basis of the method according to Example 3 ten of new substances were synthetised where 6-amino-1-hexanol (within the first group), 5-amino-1-pentanol (within the second group) as starting substances were used. These 10 substances are presented in TABLE VIII. The physicochemical charactertistics of these substances are summarised in Table XIV and Table XXV, respectively, and selected efficiency data are presented in Table XXVI.

TABLE VIII

Carbamic acid salts based on the ω-aminoalkyl alkanoates

| α,ω-amino alcohol | Carboxylic acid | Product No. | Product |
|---|---|---|---|
| 6-Amino-1-hexanol | Octanoic acid | 8.1 | Octylcarbonyloxypentylammonium octylcarbonyloxypentylcarbamate |
| | Nonanoic acid | 8.2 | Nonylcarbonyloxypentylammonium nonylcarbonyloxypentylcarbamate |
| | Decanoic acid | 8.3 | Decylcarbonyloxypentylammonium decylcarbonyloxypentylcarbamate |
| | Undecanoic acid | 8.4 | Undecylcarbonyloxypentylammonium undecylcarbonyloxypentylcarbamate |
| | Dodecanoic acid | 8.5 | Dodecylcarbonyloxypentylammonium dodecylcarbonyloxypentylcarbamate |
| 5-Amino-1-pentanol | Octanoic acid | 8.6 | Octylcarbonyloxybutylammonium octylcarbonyloxybutylcarbamate |
| | Nonanoic acid | 8.7 | Nonylcarbonoxybutylammonium nonylcarbonyloxybutylcarbamate |
| | Decanoic acid | 8.8 | Decylcarbonyloxybutylammonium decylcarbonyloxybutylcarbamate |
| | Undecanoic acid | 8.9 | Undecylcarbonyloxybutylammonium undecylcarbonyloxybutylcarbamate |
| | Dodecanoic acid | 8.10 | Dodecylcarbonyloxybutylammonium dodecylcarbonyloxybutylcarbamate |

TABLE IX

Melting point [° C.] and IR spectra of Carbamic acid salts based on the alkyl ω-aminoalkanoates (measured in KBr) [cm$^{-1}$]

| Product No. | νNH | ν$_a$CH$_3$ | ν$_a$CH$_2$ | ν$_s$CH$_2$ | υCO esters | υCO carbamates | δCH$_2$ | δCH$_3$ | ν$_a$COC | ρCH$_2$ | M.P. (° C.) |
|---|---|---|---|---|---|---|---|---|---|---|---|
| 1.1 | 3431;3355 | 2953 | 2919 | 2850 | 1734 | 1617 | 1468 | 1377 | 1194 | 721 | 45–47 |
| 1.2 | 3430;3355 | 2953 | 2919 | 2850 | 1735 | 1617 | 1468 | 1377 | 1194 | 720 | 49–50 |
| 1.3 | 3433;3355 | 2951 | 2919 | 2850 | 1735 | 1617 | 1468 | 1377 | 1194 | 719 | 51–54 |
| 1.4 | 3428;3354 | 2953 | 2919 | 2850 | 1733 | 1616 | 1468 | 1377 | 1194 | 720 | 53–55 |
| 1.5 | 3432;3355 | 2949 | 2919 | 2850 | 1735 | 1617 | 1468 | 1377 | 1193 | 720 | 56–57 |
| 1.6 | 3432;3355 | 2953 | 2920 | 2850 | 1735 | 1618 | 1468 | 1377 | 1194 | 720 | 58–60 |
| 1.7 | 3430;3355 | 2953 | 2919 | 2850 | 1735 | 1617 | 1468 | 1377 | 1194 | 720 | 61–64 |
| 1.8 | 3432;3355 | 2952 | 2919 | 2849 | 1735 | 1617 | 1468 | 1377 | 1194 | 722 | 68–71 |
| 1.9 | 3432;3365 | 2955 | 2918 | 2850 | 1735 | 1617 | 1468 | 1376 | 1194 | 720 | 86–90 |
| 1.10 | 3430;3355 | 2955 | 2920 | 2850 | 1734 | 1616 | 1468 | 1380 | 1194 | 720 | 36–40 |
| 1.11 | 3430;3350 | 2955 | 2920 | 2850 | 1734 | 1617 | 1468 | 1380 | 1194 | 720 | 38–41 |
| 1.12 | 3430;3355 | 2955 | 2920 | 2850 | 1735 | 1617 | 1468 | 1380 | 1194 | 722 | 40–43 |
| 1.13 | 3430;3355 | 2953 | 2919 | 2850 | 1735 | 1617 | 1468 | 1380 | 1194 | 720 | 42–45 |
| 1.14 | 3430;3352 | 2953 | 2920 | 2850 | 1733 | 1616 | 1468 | 1380 | 1194 | 722 | 44–47 |
| 1.15 | 3430;3355 | 2953 | 2920 | 2850 | 1733 | 1616 | 1468 | 1380 | 1194 | 722 | 46–49 |
| 1.16 | 3430;3352 | 2953 | 2918 | 2850 | 1733 | 1616 | 1469 | 1380 | 1194 | 720 | 48–51 |
| 1.17 | 3435;3353 | 2956 | 2919 | 2850 | 1734 | 1618 | 1468 | 1380 | 1194 | 720 | 50–53 |
| 1.18 | 3430;3352 | 2950 | 2920 | 2850 | 1735 | 1616 | 1468 | 1380 | 1194 | 720 | 54–57 |
| 1.19 | 3430;3352 | 2953 | 2921 | 2850 | 1730 | 1616 | 1468 | 1380 | 1194 | 722 | 58–61 |
| 1.20 | 3435;3355 | 2950 | 2919 | 2850 | 1733 | 1616 | 1468 | 1378 | 1194 | 718 | 31–34 |
| 1.21 | 3430;3350 | 2952 | 2920 | 2850 | 1735 | 1618 | 1466 | 1380 | 1194 | 720 | 33–37 |
| 1.22 | 3430;3352 | 2953 | 2920 | 2850 | 1730 | 1620 | 1468 | 1377 | 1194 | 722 | 36–40 |
| 1.23 | 3434;3353 | 2953 | 2920 | 2848 | 1736 | 1618 | 1468 | 1376 | 1194 | 720 | 38–41 |
| 1.24 | 3430;3350 | 2953 | 2922 | 2850 | 1733 | 1616 | 1469 | 1380 | 1194 | 718 | 41–44 |
| 1.25 | 3430;3355 | 2949 | 2920 | 2852 | 1734 | 1619 | 1468 | 1380 | 1194 | 722 | 43–47 |
| 1.26 | 3430;3352 | 2953 | 2920 | 2850 | 1733 | 1616 | 1468 | 1380 | 1194 | 722 | 46–49 |
| 1.27 | 3428;3352 | 2955 | 2922 | 2850 | 1730 | 1620 | 1467 | 1378 | 1192 | 719 | 50–52 |
| 1.28 | 3430;3355 | 2950 | 2918 | 2848 | 1735 | 1616 | 1468 | 1380 | 1194 | 722 | 56–59 |
| 1.29 | 3430;3350 | 2953 | 2920 | 2850 | 1735 | 1618 | 1468 | 1377 | 1194 | 723 | 58–61 |
| 1.30 | | 2993 | 2950 | 2845 | 1736 | 1612 | 1467 | 1384 | 1196 | 720 | 28–35 |
| 1.31 | | 2995 | 2952 | 2843 | 1734 | 1610 | 1468 | 1386 | 1194 | 720 | 32–37 |

TABLE X

Melting point [° C.] and IR spectra of secondary alkyl ω-aminoalkanoates (measured in CHCl$_3$) [cm$^{-1}$]

| Product No. | ν$_a$CH$_3$ | ν$_a$CH$_2$ | ν$_s$CH$_3$ | ν$_s$CH$_2$ | νCO | δCH$_2$ | δCH$_3$ | MP. [° C.] |
|---|---|---|---|---|---|---|---|---|
| 2.1 | 2982 | 2968 | 2850 | 2820 | 1720 | 1468 | 1378 | oil |
| 2.2 | 2990 | 2982 | 2850 | 2820 | 1721 | 1468 | 1376 | oil |
| 2.3 | 2993 | 2980 | 2853 | 2820 | 1720 | 1468 | 1376 | oil |
| 2.4 | 2955 | 2918 | 2850 | 2820 | 1720 | 1468 | 1376 | oil |
| 2.5 | 2965 | 2923 | 2850 | 2820 | 1720 | 1468 | 1376 | oil |
| 2.6 | 2984 | 2945 | 2850 | 2820 | 1722 | 1468 | 1376 | oil |
| 2.7 | 2965 | 2932 | 2850 | 2826 | 1723 | 1468 | 1378 | oil |
| 2.8 | 2972 | 2922 | 2850 | 2820 | 1722 | 1465 | 1379 | oil |
| 2.9 | 2958 | 2918 | 2850 | 2820 | 1720 | 1468 | 1375 | oil |
| 2.10 | 2965 | 2918 | 2850 | 2820 | 1722 | 1468 | 1373 | oil |
| 2.11 | 2958 | 2919 | 2850 | 2820 | 1721 | 1465 | 1379 | oil |
| 2.12 | 2950 | 2920 | 2850 | 2820 | 1720 | 1468 | 1376 | oil |
| 2.13 | 2950 | 2920 | 2850 | 2825 | 1720 | 1468 | 1380 | oil |
| 2.14 | 2958 | 2920 | 2850 | 2820 | 1720 | 1468 | 1378 | oil |
| 2.15 | 2956 | 2920 | 2850 | 2824 | 1720 | 1467 | 1375 | oil |
| 2.16 | 2958 | 2920 | 2848 | 2820 | 1722 | 1468 | 1378 | oil |
| 2.17 | 2958 | 2922 | 2850 | 2818 | 1720 | 1468 | 1377 | oil |
| 2.18 | 2958 | 2920 | 2850 | 2820 | 1720 | 1468 | 1378 | oil |
| 2.19 | 2962 | 2924 | 2855 | 2820 | 1719 | 1467 | 1378 | oil |
| 2.20 | 2956 | 2920 | 2850 | 2824 | 1720 | 1468 | 1380 | oil |
| 2.21 | 2966 | 2920 | 2850 | 2820 | 1725 | 1468 | 1378 | oil |
| 2.22 | 2958 | 2924 | 2850 | 2818 | 1720 | 1469 | 1378 | oil |
| 2.23 | 2954 | 2920 | 2848 | 2820 | 1726 | 1468 | 1378 | oil |
| 2.24 | 2958 | 2920 | 2850 | 2820 | 1720 | 1468 | 1378 | oil |
| 2.25 | 2959 | 2920 | 2853 | 2825 | 1723 | 1468 | 1378 | oil |
| 2.26 | 2958 | 2918 | 2850 | 2820 | 1720 | 1466 | 1375 | oil |
| 2.27 | 2956 | 2920 | 2850 | 2819 | 1720 | 1468 | 1378 | oil |
| 2.28 | 2962 | 2920 | 2853 | 2820 | 1723 | 1468 | 1377 | oil |
| 2.29 | 2960 | 2920 | 2850 | 2820 | 1724 | 1468 | 1378 | oil |
| 2.30 | 2955 | 2922 | 2854 | 2826 | 1720 | 1465 | 1378 | oil |
| 2.31 | 2959 | 2920 | 2853 | 2820 | 1722 | 1468 | 1377 | oil |
| 2.32 | 2954 | 2920 | 2852 | 2825 | 1720 | 1468 | 1378 | oil |
| 2.33 | 2956 | 2926 | 2855 | 2820 | 1720 | 1464 | 1378 | oil |
| 2.34 | 2959 | 2920 | 2850 | 2820 | 1725 | 1468 | 1380 | oil |
| 2.35 | 2958 | 2920 | 2848 | 2818 | 1720 | 1468 | 1378 | oil |
| 2.36 | 2963 | 2925 | 2853 | 2821 | 1722 | 1470 | 1378 | oil |
| 2.37 | 2958 | 2920 | 2850 | 2818 | 1720 | 1468 | 1375 | oil |
| 2.38 | 2956 | 2924 | 2847 | 2825 | 1726 | 1468 | 1378 | oil |
| 2.39 | 2958 | 2920 | 2850 | 2820 | 1720 | 1464 | 1378 | oil |

TABLE XI

Melting point [° C.] and IR spectra of the primary alkyl 6-methyl- and 6-dimethylaminohexanoates (measured in CHCl$_3$) [cm$^{-1}$]

| Product No. | ν$_a$CH$_2$ | ν$_s$CH$_3$ | ν$_s$CH$_2$ | νCO | δCH$_2$ | δCH$_3$ | M.P. [° C.] |
|---|---|---|---|---|---|---|---|
| 3.1 | 2931 | 2857 | 2801 | 1725 | 1467 | 1375 | oil |
| 3.2 | 2931 | 2857 | 2801 | 1725 | 1467 | 1376 | oil |
| 3.3 | 2929 | 2857 | 2801 | 1725 | 1467 | 1378 | oil |
| 3.4 | 2932 | 2860 | 2822 | 1725 | 1467 | 1377 | oil |
| 3.5 | 2931 | 2860 | 2822 | 1725 | 1467 | 1376 | oil |
| 3.6 | 2930 | 2859 | 2823 | 1725 | 1467 | 1376 | oil |

TABLE XI-continued

Melting point [° C.] and IR spectra of the primary alkyl 6-methyl- and 6-dimethylaminohexanoates (measured in CHCl$_3$) [cm$^{-1}$]

| Product No. | $\nu_a$CH$_2$ | $\nu_s$CH$_3$ | $\nu_s$CH$_2$ | $\nu$CO | $\delta$CH$_2$ | $\delta$CH$_3$ | M.P. [° C.] |
|---|---|---|---|---|---|---|---|
| 3.7 | 2929 | 2858 | 2823 | 1725 | 1467 | 1376 | oil |
| 3.8 | 2929 | 2858 | 2823 | 1725 | 1467 | 1376 | oil |

TABLE XII

Melting point [° C.] and IR spectra of the cycloalkyl ω-aminoalkanoates (measured in CHCl$_3$) [cm$^{-1}$]

| Product No. | $\nu_a$CH$_2$ | $\nu_s$CH$_2$ | $\nu$CO | $\delta$CH$_2$ | $\nu$COC | M.P. [° C.] |
|---|---|---|---|---|---|---|
| 5.1 | 2950 | 2870 | 1710 | 1468 | 1270; 1205 | oil |
| 5.2 | 2960 | 2880 | 1710 | 1468 | 1250; 1205 | oil |
| 5.3 | 2950 | 2880 | 1710 | 1468 | 1270, 1205 | oil |
| 5.4 | 2950 | 2870 | 1710 | 1468 | 1270, 1205 | oil |
| 5.5 | 2950 | 2875 | 1710 | 1468 | 1260, 1205 | oil |
| 5.6 | 2950 | 2870 | 1710 | 1468 | 1270, 1205 | oil |
| 5.7 | 2950 | 2870 | 1710 | 1468 | 1270, 1205 | oil |
| 5.8 | 2950 | 2875 | 1710 | 1468 | 1270, 1210 | oil |
| 5.9 | 2950 | 2870 | 1710 | 1468 | 1270, 1205 | oil |

TABLE XIII

Melting point [° C.] and IR spectra of the Carbamic acid salts based on the cycloalkyl ω-aminoalkanoates (measured in KBr) [cm$^{-1}$]

| Product No. | $\nu$NH | $\nu_a$CH$_2$ | $\nu_s$CH$_2$ | $\nu$CO esters | $\nu$CO carbamates | $\delta$CH$_2$ | $\nu_a$COC | $\rho$CH$_2$ | M.P. (° C.) |
|---|---|---|---|---|---|---|---|---|---|
| 4.1 | 3430;3363 | 2920 | 2848 | 1734 | 1617 | 1468 | 1194 | 721 | 50–55 |
| 4.2 | 3430;3363;3112 | 2920 | 2848 | 1735 | 1615 | 1468 | 1194 | 720 | 76–80 |
| 4.3 | 3443;3342 | | 2848 | 1735 | 1615 | 1468 | 1194 | 721 | 15–20 |
| 4.4 | 3430;3363 | 2918 | 2848 | 1736 | 1617 | 1468 | 1194 | 721 | 47–52 |
| 4.5 | 3430;3363;3112 | 2920 | 2848 | 1735 | 1617 | 1467 | 1194 | 720 | 71–75 |
| 4.6 | 3443;3342 | | 2850 | 1735 | 1615 | 1468 | 1194 | 721 | 17–22 |
| 4.7 | 3430;3363 | 2920 | 2849 | 1735 | 1619 | 1468 | 1194 | 721 | 43–48 |
| 4.8 | 3430;3363;3110 | 2920 | 2848 | 1737 | 1617 | 1467 | 1194 | 722 | 68–72 |
| 4.9 | 3430;3342 | | 2850 | 1735 | 1617 | 1468 | 1194 | 720 | 20–25 |

TABLE XIV

Melting point [° C.] and IR spectra of the Carbamic acid salts based on the ω-aminoalkyl alkanoates (measured in KBr) [cm$^{-1}$]

| Product No. | $\nu$NH | $\nu_a$CH$_3$ | $\nu_a$CH$_2$ | $\nu$CO esters | $\nu$CO carbamates | $\delta$CH$_2$ | $\delta$CH$_3$ | $\nu_a$COC | $\rho$CH$_2$ | M.P. (° C.) |
|---|---|---|---|---|---|---|---|---|---|---|
| 8.1 | 3430;3346 | 2995 | 2955 | 1735 | 1617 | 1468 | 1376 | 1194 | 720 | 46–50 |
| 8.2 | 3430;3352 | 2995 | 2955 | 1735 | 1620 | 1468 | 1377 | 1194 | 720 | 51–54 |
| 8.3 | 3433;3350 | 2992 | 2945 | 1734 | 1617 | 1468 | 1377 | 1194 | 719 | 55–59 |
| 8.4 | 3428;3348 | 2995 | 2955 | 1733 | 1616 | 1468 | 1378 | 1194 | 720 | 64–66 |
| 8.5 | 3432;3350 | 2995 | 2960 | 1735 | 1617 | 1467 | 1377 | 1193 | 720 | 65–68 |
| 8.6 | 3432;3346 | 2990 | 2955 | 1736 | 1618 | 1468 | 1376 | 1194 | 720 | 63–65 |
| 8.7 | 3430;3346 | 2995 | 2955 | 1735 | 1617 | 1468 | 1377 | 1194 | 720 | 60–62 |
| 8.8 | 3432;3350 | 2995 | 2950 | 1735 | 1617 | 1468 | 1377 | 1195 | 722 | 58–59 |
| 8.9 | 3428;3365 | 2995 | 2955 | 1735 | 1617 | 1468 | 1376 | 1194 | 720 | 55–57 |
| 8.10 | 3430;3355 | 2994 | 2955 | 1734 | 1616 | 1468 | 1380 | 1194 | 722 | 52–54 |

TABLE XV

Melting point [° C.] and IR spectra of the primary alkyl ω-acetylaminoalkanoates (measured in KBr) [cm$^{-1}$]

| Product No. | vNH | v$_a$CH$_3$ | v$_a$CH$_2$ | vCO ester | vCO amide | δNH amide | vCOC | M.P. [° C.] |
|---|---|---|---|---|---|---|---|---|
| 6.1 | 3450 | 2980 | 2950 | 1735 | 1665 | 1520 | 1185;1250 | 34–37 |
| 6.2 | 3455 | 2980 | 2950 | 1735 | 1665 | 1520 | 1187;1250 | 36–40 |
| 6.3 | 3450 | 2980 | 2955 | 1734 | 1665 | 1520 | 1185;1250 | 38–42 |
| 6.4 | 3450 | 2980 | 2950 | 1735 | 1668 | 1525 | 1180;1250 | 40–45 |
| 6.5 | 3455 | 2980 | 2950 | 1735 | 1665 | 1518 | 1185;1250 | 44–48 |
| 6.6 | 3450 | 2950 | 2870 | 1720 | 1660 | 1520 | 1250;1185 | 25–27 |
| 6.7 | 3450 | 2950 | 2870 | 1720 | 1660 | 1520 | 1250;1185 | 34–36 |
| 6.8 | 3450 | 2950 | 2870 | 1720 | 1660 | 1520 | 1250;1185 | 38–39 |
| 6.9 | 3450 | 2950 | 2870 | 1720 | 1660 | 1520 | 1250;1185 | 46–48 |
| 6.10 | 3450 | 2950 | 2865 | 1720 | 1660 | 1520 | 1250;1185 | 53–56 |
| 6.11 | 3450 | 2950 | 2870 | 1720 | 1665 | 1520 | 1250;1185 | 60–62 |
| 6.12 | 3450 | 2950 | 2870 | 1720 | 1660 | 1520 | 1250;1185 | 66–70 |
| 6.13 | 3450 | 2945 | 2870 | 1719 | 1660 | 1520 | 1250;1185 | oil |
| 6.14 | 3450 | 2950 | 2870 | 1720 | 1660 | 1520 | 1240;1185 | 29–33 |
| 6.15 | 3455 | 2950 | 2870 | 1720 | 1665 | 1518 | 1250;1185 | 32–35 |
| 6.16 | 3450 | 2950 | 2870 | 1717 | 1660 | 1520 | 1250;1185 | 33–37 |
| 6.17 | 3450 | 2950 | 2870 | 1720 | 1664 | 1525 | 1252;1185 | 36–40 |
| 6.18 | 3454 | 2950 | 2870 | 1720 | 1665 | 1520 | 1250;1185 | 46–49 |
| 6.19 | 3454 | 2950 | 2870 | 1720 | 1660 | 1520 | 1250;1185 | 47–50 |
| 6.20 | 3450 | 2950 | 2870 | 1720 | 1665 | 1520 | 1250;1190 | 28–31 |
| 6.21 | 3450 | 2945 | 2870 | 1720 | 1660 | 1520 | 1250;1185 | 37–39 |
| 6.22 | 3450 | 2950 | 2870 | 1723 | 1660 | 1518 | 1250;1185 | 51–54 |
| 6.23 | 3450 | 2950 | 2870 | 1720 | 1655 | 1520 | 1250;1185 | 47–49 |

TABLE XVI

Melting point [° C.] and IR spectra of the secondary alkyl ω-acetylaminoalkanoates (measured in CHCl$_3$) [cm$^{-1}$]

| Product No. | vNH | v$_a$CH$_2$ | vCO ester | vCO amide | δNH amide | vCOC | M.P. [° C.] |
|---|---|---|---|---|---|---|---|
| 7.1 | 3450 | 2950 | 1735 | 1665 | 1520 | 1185;1250 | oil |
| 7.2 | 3455 | 2950 | 1735 | 1665 | 1520 | 1187;1250 | oil |
| 7.3 | 3450 | 2955 | 1734 | 1665 | 1520 | 1185;1250 | oil |
| 7.4 | 3450 | 2950 | 1735 | 1668 | 1525 | 1180;1250 | oil |
| 7.5 | 3455 | 2950 | 1735 | 1665 | 1518 | 1185;1250 | oil |
| 7.6 | 3450 | 2870 | 1720 | 1660 | 1520 | 1250;1185 | oil |
| 7.7 | 3450 | 2870 | 1720 | 1660 | 1520 | 1250;1185 | oil |
| 7.8 | 3450 | 2870 | 1720 | 1660 | 1520 | 1250;1185 | oil |
| 7.9 | 3450 | 2870 | 1720 | 1660 | 1520 | 1250;1185 | oil |
| 7.10 | 3450 | 2865 | 1720 | 1660 | 1520 | 1250;1185 | oil |
| 7.11 | 3454 | 2870 | 1725 | 1665 | 1520 | 1250;1185 | oil |
| 7.12 | 3450 | 2870 | 1720 | 1660 | 1520 | 1250;1185 | oil |
| 7.13 | 3450 | 2870 | 1719 | 1660 | 1520 | 1250;1185 | oil |
| 7.14 | 3450 | 2870 | 1720 | 1660 | 1520 | 1240;1185 | oil |
| 7.15 | 3455 | 2870 | 1720 | 1665 | 1518 | 1255;1178 | oil |
| 7.16 | 3450 | 2870 | 1724 | 1660 | 1520 | 1250;1185 | oil |
| 7.17 | 3450 | 2870 | 1720 | 1664 | 1525 | 1252;1185 | oil |
| 7.18 | 3454 | 2870 | 1720 | 1665 | 1520 | 1250;1185 | oil |
| 7.19 | 3454 | 2870 | 1720 | 1660 | 1520 | 1250;1185 | oil |
| 7.20 | 3450 | 2870 | 1720 | 1665 | 1520 | 1250;1190 | oil |
| 7.21 | 3450 | 2868 | 1720 | 1665 | 1520 | 1250;1185 | oil |
| 7.22 | 3450 | 2870 | 1723 | 1660 | 1518 | 1250;1185 | oil |
| 7.23 | 3450 | 2870 | 1720 | 1665 | 1520 | 1250;1190 | oil |
| 7.24 | 3450 | 2870 | 1720 | 1665 | 1520 | 1250;1190 | oil |
| 7.25 | 3450 | 2870 | 1720 | 1665 | 1520 | 1250;1190 | oil |
| 7.26 | 3450 | 2875 | 1720 | 1660 | 1520 | 1250;1190 | oil |
| 7.27 | 3450 | 2870 | 1720 | 1665 | 1515 | 1250;1190 | oil |
| 7.28 | 3450 | 2865 | 1720 | 1665 | 1520 | 1250;1190 | oil |
| 7.29 | 3450 | 2870 | 1720 | 1665 | 1520 | 1250;1185 | oil |
| 7.30 | 3450 | 2870 | 1720 | 1674 | 1520 | 1250;1190 | oil |
| 7.31 | 3450 | 2870 | 1720 | 1655 | 1518 | 1245;1190 | oil |
| 7.32 | 3460 | 2870 | 1720 | 1660 | 1520 | 1254;1190 | oil |
| 7.33 | 3450 | 2870 | 1720 | 1665 | 1520 | 1250;1190 | oil |
| 7.34 | 3450 | 2870 | 1728 | 1665 | 1520 | 1250;1190 | oil |
| 7.35 | 3450 | 2870 | 1720 | 1660 | 1520 | 1250;1194 | oil |
| 7.36 | 3450 | 2865 | 1720 | 1667 | 1520 | 1250;1190 | oil |

TABLE XVII

1H NMR spectra of secondary alkyl ω-aminoalkanoates

| No. | 3H CH$_3$ | 3H CH$_3$ | n.H CH$_2$* | 2H CH$_2$CO | 2H CH$_2$NH$_2$ | 1H CHO | 2H NH$_2$ |
|---|---|---|---|---|---|---|---|
| 2.1 | 0.89t, J=6 | 1.20d, J=6 | 1.23qs, 8H(4); 1.50m, 6H(3) | 2.29t, J=7 | 2.73bs | 4.91m | 2.39bs |
| 2.2 | 0.88t, | 0.95t, | 1.20–1.80m, | 2.30t, | 2.79bs | 4.82m | — |

TABLE XVII-continued

1H NMR spectra of secondary alkyl ω-aminoalkanoates

| No. | 3H CH$_3$ | 3H CH$_3$ | n.H CH$_2$* | 2H CH$_2$CO | 2H CH$_2$NH$_2$ | 1H CHO | 2H NH$_2$ |
|---|---|---|---|---|---|---|---|
| 2.3 | 0.90t, J=6.5 | 0.90t, J=6.5 | 1.25–1.80m, 16H(3+3+1+NH$_2$) | 2.30t, J=6.5 | 2.79bs | 4.91m | — |
| 2.4 | 0.88t, J=6.5 | 1.19d, J=6 | 1.27qs, 10H(5); 1.46m, 6H(3) | 2.30t, J=7 | 2.77bs | 4.90m | 3.33bs |
| 2.5 | 0.88t, J=6 | 0.88t, J=6 | 1.25–1.80m, 16H(2+2+3+NH$_2$) | 2.31t, J=6 | 2.72bs | 4.82m | — |
| 2.6 | 0.88t, J=7 | 1.20d, J=7 | 1.28qs, 12H(6); 1.46m, 6H(3) | 2.30t, J=7 | 2.73bs | 4.92m | 1.96bs |
| 2.7 | 0.89t, J=6 | 0.89t, J=6 | 1.20–1.80m, 18H(4+3+1+NH$_2$) | 2.32t, J=6 | 2.74bs | 4.84m | — |
| 2.8 | 0.89t, J=7 | 0.89t, J=7 | 1.25–1.80m, 20H(5+3+1+NH$_2$) | 2.31t, J=6 | 2.95bs | 4.87m | — |
| 2.9 | 0.89t, J=6.5 | 0.89t, J=6.5 | 1.25–1.80m, 20H(4+3+2+NH$_2$) | 2.31t, J=6.5 | 2.73bs | 4.90m | — |
| 2.10 | 0.89t, J=65 | 1.21d, J=6.5 | 1.29qs, 14H(7); 1.46m, 6H(3) | 2.30t, J=7 | 2.72bs | 4.92m | 1.77bs |
| 2.11 | 0.89t, J=6 | 1.19d, J=6 | 1.28qs, 16H(8); 1.46m, 6H(3) | 2.30t, J=7 | 2.74bs | 4.91m | Překryt (CH$_2$)$_3$ |
| 2.12 | 0.88t, J=6.5 | 1.20d, J=6.5 | 1.28qs, 18H(9); 1.46m, 6H(3) | 2.31t, J=6.5 | 2.73bs | 4.91m | 1.77bs |
| 2.13 | 0.89t, J=6 | 0.89t, J=6 | 1.25–1.80m, 30H(6+5+3+NH$_2$) | 2.30t, J=6.5 | 2.72bs | 4.91m | — |
| 2.14 | 0.88t, J=6 | 1.20d, J=6 | 1.27qs, 8H(4); 1.46m, 8H(4) | 2.31t, J=6.5 | 2.72bs | 4.90m | 1.80bs |
| 2.15 | 0.89t, J=6.5 | 0.89t, J=6.5 | 1.20–1.80m, 18H(4+3+1+NH$_2$) | 2.31t, J=6.5 | 2.74bs | 4.91m | — |
| 2.16 | 0.89t, J=6 | 0.89t, J=6 | 1.20–1.80m, 18H(4+2+2+NH$_2$) | 2.30t, J=7 | 2.73bs | 4.92m | — |
| 2.17 | 0.88t, J=6.5 | 1.21d, J=6.5 | 1.28qs, 10H(5); 1.46m, 8H(4) | 2.31t, J=6.5 | 2.72bs | 4.91m | 1.85bs |
| 2.18 | 0.89t, J=6 | 0.89t, J=6 | 1.20–1.80m, 20H(4+4+1+NH$_2$) | 2.31t, J=6.5 | 2.73bs | 4.90m | — |
| 2.19 | 0.89t, J=6.5 | 1.20d, J=6.5 | 1.29qs, 12H(6); 1.46m, 8H(4) | 2.32t, J=6.5 | 2.74bs | 4.92m | 1.80bs |
| 2.20 | 0.88t, J=7 | 0.88t, J=7 | 1.20–1.80m, 22H(5+4+1+NH$_2$) | 2.30t, J=6 | 2.73bs | 4.92m | — |
| 2.21 | 0.89t, J=6.5 | 0.89t, J=6.5 | 1.20–1.80m, 22H(4+4+2+NH$_2$) | 2.31t, J=6.5 | 2.73bs | 4.91m | — |
| 2.22 | 0.89t, J=6 | 0.89t, J=6 | 1.20–1.80m, 22H(4+3+3+NH$_2$) | 2.32t, J=6.5 | 2.73bs | 4.90m | — |
| 2.23 | 0.89t, J=6.5 | 1.21d, J=6.5 | 1.29qs, 14H(7); 1.46m, 8H(4) | 2.31t, J=6.5 | 2.72bs | 4.92m | 1.77bs |
| 2.24 | 0.89t, J=6 | 1.20d, J=6 | 1.28qs, 16H(8); 1.46m, 8H(4) | 2.30t, J=6.5 | 2.73bs | 4.91m | 1.80bs |
| 2.25 | 0.88t, J=6 | 1.21d, J=6 | 1.29qs, 18(9); 1.46m, 8H(4) | 2.31t, J=6.5 | 2.74bs | 4.92m | 1.80bs |
| 2.26 | 0.89t, J=6.5 | 0.89t, J=6.5 | 1.20–1.80m, 32H(6+5+4+NH$_2$) | 2.32t, 3=6.5 | 2.73bs | 4.90m | — |
| 2.27 | 0.89t, J=6 | 1.20d, J=6 | 1.28qs, 10H(4); 1.46m, 8H(4) | 2.32t, J=6.5 | 2.72bs | 4.90m | 1.80bs |
| 2.28 | 0.89t, J=6.5 | 0.89t, J=6.5 | 1.20–1.80m, 20H(4+3+I+NH$_2$) | 2.32t, J=6.5 | 2.73bs | 4.92m | — |
| 2.29 | 0.89t, J=6.5 | 0.89t, J=6.5 | 1.20–1.80m, 20H(4+2+2+NH$_2$) | 2.32t, J=7 | 2.74bs | 4.92m | — |
| 2.30 | 0.88t, J=6 | 1.20d, J=6 | 1.28qs, 10H(5); 1.46m, 10H(5) | 2.32t, J=6.5 | 2.73bs | 4.91m | 1.85bs |
| 2.31 | 0.89t, J=6.5 | 0.89t, J=6.5 | 1.20–1.80m, 22H(5+4+1+NH$_2$) | 2.31t, J=6.5 | 2.72bs | 4.91m | — |
| 2.32 | 0.88t, J=6.5 | 1.21d, J=6.5 | 1.29qs, 12H(6); 1.46m, 10H(5) | 2.30t, J=6.5 | 2.73bs | 4.92m | 1.85bs |
| 2.33 | 0.88t, J=6 | 0.88t, J=6 | 1.20–1.80m, 24H(5+5+1+NH$_2$) | 2.32t, J=6.5 | 2.73bs | 4.90m | — |
| 2.34 | 0.88t, J=7 | 0.88t, J=7 | 1.20–1.80m, 24H(5+4+2+NH$_2$) | 2.31t, J=6 | 2.73bs | 4.92m | — |
| 2.35 | 0.90t, J=6.5 | 0.90t, J=6.5 | 1.20–1.80m, 24H(5+3+3+NH$_2$) | 2.30t, J=6.5 | 2.73bs | 4.87m | — |
| 2.36 | 0.89t, J=6.5 | 1.20d, J=6.5 | 1.28qs, 14H(7); 1.46m, 10H(5) | 2.32t, J=6.5 | 2.74bs | 4.92m | 1.80bs |
| 2.37 | 0.89t, J=6.5 | 1.21d, J=6.5 | 1.29qs, 16H(8); 1.46m, 10H(5) | 2.32t, J=6.5 | 2.72bs | 4.90m | 1.77bs |
| 2.38 | 0.88t, J=6 | 1.20d, J=6 | 1.28qs, 18(9); 1.46m, 10H(5) | 2.30t, J=6.5 | 2.72bs | 4.92m | 1.80bs |
| 2.39 | 0.89t, | 0.89t, | 1.20–1.80m, | 2.31t, | 2.73bs | 4.91m | — |

TABLE XVII-continued

1H NMR spectra of secondary alkyl ω-aminoalkanoates

| No. | 3H CH$_3$ | 3H CH$_3$ | n.H CH$_2$* | 2H CH$_2$CO | 2H CH$_2$NH$_2$ | 1H CHO | 2H NH$_2$ |
|---|---|---|---|---|---|---|---|
| | J=6.5 | J=6.5 | 34H(6+5+5+NH$_2$) | J=6.5 | | | |

*n is number of H;
figure in bracket is number of CH$_2$ groups

TABLE XVIII

1H NMR spectra of primary alkyl 6-methyl- and 6-dimethylaminohexanoates

| No. | 3H CH$_3$ | n.H CH$_3$ | n.H CH$_2$ | 2H CH$_2$CO | 2H CH$_2$O |
|---|---|---|---|---|---|
| 3.1 | 0.89t, J=6 | 2.38s, 3H | 1.20–1.80m, 20H(4+6) | 2.32t, J=6.5 | 4.07t, J=7 |
| 3.2 | 0.88t, J=6 | 2.37s, 3H | 1.20–1.80m, 22H(4+7) | 2.31t, J=6.5 | 4.07t, J=7 |
| 3.3 | 0.88t, J=6 | 2.38s, 3H | 1.20–1.80m, 24H(4+8) | 2.32t, J=6.5 | 4.06t, J=7 |
| 3.4 | 0.89t, J=6 | 2.25s, 6H | 1.20–1.80m, 20H(4+6) | 2.32t, J=6.5 | 4.07t, J=7 |
| 3.5 | 0.88t, J=6 | 2.26s, 6H | 1.20–1.80m, 22H(4+7) | 2.32t, J=6.5 | 4.06t, J=7 |
| 3.6 | 0.88t, J=6 | 2.26s, 6H | 1.20–1.80m, 24H(4+8) | 2.31t, J=6.5 | 4.06t, J=7 |
| 3.7 | 0.89t, J=6 | 2.26s, 6H | 1.20–1.80m, 26H(4+9) | 2.32t, J=6.5 | 4.07t, J=7 |
| 3.8 | 0.89t, J=6 | 2.26s, 6H | 1.20–1.80m, 28H(4+10) | 2.31t, J=6.5 | 4.07t, J=7 |

*n is number of H;
figure in bracket is number of CH$_2$ groups

TABLE XIX

1H NMR spectra of cycloalkyl ω-aminoalkanoates

| No. | n.H CH$_2$* | 2H CH$_2$CO | 2H CH$_2$NH$_2$ | 1H CHO |
|---|---|---|---|---|
| 5.1 | 1.55–1.80m, 16H(4+3+NH$_2$) | 2.29t, J=7 | 2.80bs | 4.94m |
| 5.2 | 1.55–1.80m, 18H(5+3+NH$_2$) | 2.29t, J=7 | 2.82bs | 4.93m |
| 5.3 | 1.53–1.80m, 20H(6+3+NH$_2$) | 2.29t, J=7 | 2.80bs | 4.95m |
| 5.4 | 1.53–1.80m, 22H(7+3+NH$_2$) | 2.29t, J=7 | 2.70bs | 5.00m |
| 5.5 | 1.55–1.80m, 20H(5+4+NH$_2$) | 2.29t, J=7 | 2.80bs | 4.95m |
| 5.6 | 1.55–1.80m, 22H(6+4+NH$_2$) | 2.29t, J=7 | 2.80bs | 4.94m |
| 5.7 | 1.53–1.80m, 24H(7+4+NH$_2$) | 2.29t, J=7 | 2.82bs | 4.95m |
| 5.8 | 1.55–1.80m, 24H(7+5+NH$_2$) | 2.29t, J=7 | 2.80bs | 4.95m |
| 5.9 | 1.55–1.80m, 26H(8+5+NH$_2$) | 2.29t, J=7 | 2.82bs | 4.93m |

*n is number of H;
figure in bracket is number of CH$_2$ groups

TABLE XX

1H NMR spectra of alkyl ω-acetylaminoalkanoates

| No. | 3H CH$_3$ | n.H CH$_2$* | 3H CH$_3$CO | 2H CH$_2$CO | 2H CH$_2$NH | 2H CH$_2$O | 1H NH |
|---|---|---|---|---|---|---|---|
| 6.1 | 0.89t, J=6 | 1.28qs, 12H(6); 1.51m, 4H(2) | 1.94s | 2.30t, J=6.5 | 3.24m | 4.07t, J=7 | 5.62bs |
| 6.2 | 0.88t, J=6 | 1.29qs, 14H(7); 1.50m, 4H(2) | 1.95s | 2.30t, J=6.5 | 3.24m | 4.06t, J=7 | 5.66bs |
| 6.3 | 0.89t, J=6 | 1.29qs, 16H(8); 1.51m, 4H(2) | 1.95s | 2.31t, J=6.5 | 3.26m | 4.07t, J=7 | 5.66bs |
| 6.4 | 0.89t, J=6 | 1.28qs, 18H(9); 1.51m, 4H(2) | 1.94s | 2.30t, J=6.5 | 3.25m | 4.07t, J=7 | 5.62bs |
| 6.5 | 0.88t, J=6 | 1.29qs, 20H(10); 1.50m, 4H(2) | 1.96s | 2.30t, J=6.5 | 3.24m | 4.06t, J=7 | 5.69bs |
| 6.6 | 0.89t, J=6 | 1.28qs, 8H(4); 1.51m, 6H(3) | 1.95s | 2.31t, J=6.5 | 3.25m | 4.07t, J=7 | 5.66bs |
| 6.7 | 0.88t, J=6 | 1.29qs, 10H(5); 1.51m, 6H(3) | 1.94s | 2.30t, J=6.5 | 3.26m | 4.06t, J=7 | 5.69bs |
| 6.8 | 0.88t, J=6 | 1.29qs, 12H(6); 1.51m, 6H(3) | 1.95s | 2.31t, J=6.5 | 3.25m | 4.07t, J=7 | 5.69bs |
| 6.9 | 0.89t, J=6 | 1.29qs, 14H(7); 1.50m, 6H(3) | 1.94s | 2.31t, J=6.5 | 3.25m | 4.06t, J=7 | 5.72bs |
| 6.10 | 0.88t, J=6 | 1.29qs, 16H(8); 1.50m, 6H(3) | 1.95s | 2.31t, J=6.5 | 3.25m | 4.06t, J=7 | 5.66bs |
| 6.11 | 0.88t, J=6 | 1.28qs, 18H(9); 1.50m, 6H(3) | 1.95s | 2.31t, J=6.5 | 3.25m | 4.06t, J=7 | 5.69bs |

TABLE XX-continued

1H NMR spectra of alkyl ω-acetylaminoalkanoates

| No. | 3H CH$_3$ | n.H CH$_2$* | 3H CH$_3$CO | 2H CH$_2$CO | 2H CH$_2$NH | 2H CH$_2$O | 1H NH |
|---|---|---|---|---|---|---|---|
| 6.12 | 0.89t, J=6 | 1.28qs, 20H(10); 1.50m, 6H(3) | 1.96s | 2.31t, J=6.5 | 3.24m | 4.07t, J=7 | 5.6lbs |
| 6.13 | 0.88t, J=6 | 1.28qs, 6H(3); 1.51m, 8H(4) | 1.94s | 2.31t, J=6.5 | 3.25m | 4.07t, J=7 | 5.66bs |
| 6.14 | 0.89t, J=6 | 1.28qs, 10H(5); 1.51m, 8H(4) | 1.94s | 2.30t, J=6.5 | 3.26m | 4.06t, J=7 | 5.69bs |
| 6.15 | 0.88t, J=6 | 1.29qs, 12H(6); 1.50m, 8H(4) | 1.95s | 2.31t, J=6.5 | 3.25m | 4.06t, J=7 | 5.61bs |
| 6.16 | 0.88t, J=6 | 1.28qs, 14H(7); 1.51m, 8H(4) | 1.96s | 2.31t, J=6.5 | 3.24m | 4.06t, J=7 | 5.69bs |
| 6.17 | 0.88t, J=6 | 1.29qs, 16H(8); 1.50m, 8H(4) | 1.96s | 2.30t, J=6.5 | 3.24m | 4.07t, J=7 | 5.69bs |
| 6.18 | 0.89t, J=6 | 1.29qs, 18H(9); 1.50m, 8H(4) | 1.94s | 2.31t, J=6.5 | 3.26m | 4.07t, J=7 | 5.66bs |
| 6.19 | 0.88t, J=6 | 1.28qs, 20H(10); 1.50m, 8H(4) | 1.94s | 2.31t, J=6.5 | 3.25m | 4.07t, J=7 | 5.69bs |
| 6.20 | 0.89t, J=6 | 1.29qs, 6H(3); 1.50m, 10H(5) | 1.94s | 2.30t, J=6.5 | 3.25m | 4.07t, J=7 | 5.72bs |
| 6.21 | 0.89t, J=6 | 1.29qs, 12H(6); 1.51m, 10H(5) | 1.96s | 2.30t, J=6.5 | 3.26m | 4.06t, J=7 | 5.69bs |
| 6.22 | 0.88t, J=6 | 1.28qs, 16H(8); 1.51m, 10H(5) | 1.95s | 2.31t, J=6.5 | 3.26m | 4.07t, J=7 | 5.66bs |
| 6.23 | 0.89t, J=6 | 1.28qs, 20H(10); 1.50m, 10H(5) | 1.95s | 2.31t, J=6.5 | 3.24m | 4.06t, J=7 | 5.69bs |

*n is number of H;
figure in bracket is number of CH$_2$ groups

TABLE XXI

1H NMR spectra of secondary alkyl ω-acetylaminoalkanoates

| No. | 3H CH$_3$ | 3H CH$_3$ | n.H CH$_2$* | 3H CH$_3$CO | 2H CH$_2$CO | 2H CH$_2$NH | 1H CHO | 1H NH |
|---|---|---|---|---|---|---|---|---|
| 7.1 | 0.89t, J=6 | 1.20d, J=6 | 1.20–1.80m, 12H(2+4) | 1.97s | 2.32t, J=6.5 | 3.25m | 4.91m | 5.85bs |
| 7.2 | 0.87t, J=6.5 | 0.95t, J=6.5 | 1.20–1.80m, 12H(3+2+1) | 1.97s | 2.33t, J=6.5 | 3.26m | 4.82m | 5.91bs |
| 7.3 | 0.89t, J=6 | 1.21d, J=6 | 1.20–1.80m, 14H(2+5) | 1.97s | 2.31t, J=6.5 | 3.25m | 4.91m | 5.74bs |
| 7.4 | 0.88t, J=6 | 1.21d, J=6 | 1.20–1.80m, 16H(2+6) | 1.97s | 2.31t, J=6.5 | 3.26m | 4.91m | 5.79bs |
| 7.5 | 0.87t, J=6.5 | 0.94t, J=6.5 | 1.20–1.80m, 16H(5+2+1) | 1.97s | 2.33t, J=6.5 | 3.27m | 4.82m | 5.70bs |
| 7.6 | 0.89t, J=6.5 | 1.20d, J=6.5 | 1.20–1.80m, 18H(2+7) | 1.97s | 2.32t, J=6.5 | 3.26m | 4.82m | 5.79bs |
| 7.7 | 0.87t, J=6 | 1.21d, J=6 | 1.20–1.80m, 14H(3+4) | 1.97s | 2.31t, J=6.5 | 3.27m | 4.91m | 5.79bs |
| 7.8 | 0.88t, J=6.5 | 0.95t, J=6.5 | 1.20–1.80m, 14H(3+2+2) | 1.97s | 2.33t, J=6.5 | 3.25m | 4.82m | 5.85bs |
| 7.9 | 0.89t, J=6 | 1.21d, J=6 | 1.20–1.80m, 16H(3+5) | 1.97s | 2.31t, J=6.5 | 3.26m | 4.91m | 5.79bs |
| 7.10 | 0.87t, J=6.5 | 0.94t, J=6.5 | 1.20–1.80m, 16H(3+4+1) | 1.97s | 2.32t, J=6.5 | 3.27m | 4.82m | 5.79bs |
| 7.11 | 0.88t, J=6.5 | 0.95t, J=6.5 | 1.20–1.80m, 18H(3+4+2) | 1.97s | 2.33t, J=6.5 | 3.25m | 4.82m | 5.85bs |
| 7.12 | 0.87t, J=6.5 | 0.94t, J=6.5 | 1.20–1.80m, 18H(3+3+3) | 1.97s | 2.33t, J=6.5 | 3.27m | 4.91m | 5.85bs |
| 7.13 | 0.88t, J=6 | 1.20d, J=6 | 1.20–1.80m, 20H(3+7) | 1.97s | 2.31t, J=6.5 | 3.25m | 4.82m | 5.79bs |
| 7.14 | 0.89t, J=6 | 1.21d, J=6 | 1.20–1.80m, 22H(3+8) | 1.97s | 2.32t, J=6.5 | 3.26m | 4.82m | 5.79bs |
| 7.15 | 0.88t, J=6.5 | 0.88t, J=6.5 | 1.20–1.80m, 28H(3+11) | 1.96s | 2.31t, J=6.5 | 3.25m | 4.91m | 5.79bs |
| 7.16 | 0.89t, J=6 | 1.20d, J=6 | 1.20–1.80m, 16H(4+4) | 1.96s | 2.28t, J=6.5 | 3.24m | 4.91m | 5.60bs |
| 7.17 | 0.88t, J=6.5 | 0.95t, J=6.5 | 1.20–1.80m, 16H(4+3+1) | 1.97s | 2.30t, J=6.5 | 3.24m | 4.82m | 5.65bs |
| 7.18 | 0.90t, J=6.5 | 0.90t, J=6.5 | 1.10–1.80m, 16H(4+2+2) | 1.96s | 2.30t, J=6.5 | 3.23m | 4.91m | 5.95bs |
| 7.19 | 0.89t, | 1.20d, | 1.20–1.80m, | 1.97s | 2.27t, | 3.24m | 4.91m | 5.79bs |

TABLE XXI-continued

1H NMR spectra of secondary alkyl ω-acetylaminoalkanoates

| No. | 3H CH$_3$ | 3H CH$_3$ | n.H CH$_2$* | 3H CH$_3$CO | 2H CH$_2$CO | 2H CH$_2$NH | 1H CHO | 1H NH |
|---|---|---|---|---|---|---|---|---|
| 7.20 | 0.88t, J=6.5 | 0.95t, J=6.5 | 1.20–1.80m, 18H(4+5) | 1.97s | 2.30t, J=6.5 | 3.23m | 4.82m | 5.65bs |
| 7.21 | 0.88t, J=6.5 | 0.95t, J=6.5 | 1.20–1.80m, 18H(4+4+1) | 1.97s | 2.30t, J=6.5 | 3.23m | 4.82m | 5.65bs |
| 7.22 | 0.88t, J=6.5 | 0.95t, J=6.5 | 1.20–1.80m, 20H(4+6) | 1.97s | 2.30t, J=6.5 | 3.23m | 4.82m | 5.65bs |
| 7.23 | 0.87t, J=6.5 | 0.94t, J=6.5 | 1.20–1.80m, 20H(4+5+1) | 1.97s | 2.32t, J=6.5 | 3.24m | 4.82m | 5.65bs |
| 7.24 | 0.88t, J=6.5 | 0.95t, J=6.5 | 1.20–1.80m, 20H(4+4+2) | 1.97s | 2.30t, J=6.5 | 3.23m | 4.82m | 5.65bs |
| 7.25 | 0.88t, J=6 | 1.20d, J=6 | 1.20–1.80m, 20H(4+3+3) | 1.96s | 2.30t, J=6.5 | 3.24m | 4.91m | 5.67bs |
| 7.26 | 0.88t, J=6 | 1.21d, J=6 | 1.20–1.80m, 22H(4+7) | 1.97s | 2.28t, J=6.5 | 3.22m | 4.82m | 5.68bs |
| 7.27 | 0.89t, J=6 | 1.19d, J=6 | 1.20–1.80m, 24H(4+8) | 1.96s | 2.27t, J=6.5 | 3.23m | 4.91m | 5.64bs |
| 7.28 | 0.89t, J=6.5 | 0.95t, J=6.5 | 1.20–1.80m, 18H(5+4) | 1.97s | 2.30t, J=6.5 | 3.23m | 4.82m | 5.67bs |
| 7.29 | 0.90t, J=6.5 | 0.90t, J=6.5 | 1.20–1.80m, 18H(5+3+1) | 1.97s | 2.28t, J=6.5 | 3.23m | 4.92m | 5.68bs |
| 7.30 | 0.88t, J=6 | 1.19d, J=6 | 1.20–1.80m, 18H(5+2+2) | 1.96s | 2.26t, J=6.5 | 3.23m | 4.90m | 5.72bs |
| 7.31 | 0.88t, J=6.5 | 0.88t, J=6.5 | 1.20–1.80m, 20H(5+5) | 1.97s | 2.29t, J=6.5 | 3.22m | 4.81m | 5.73bs |
| 7.32 | 0.88t, J=6 | 1.19t, J=6 | 1.20–1.80m, 20H(5+4+1) | 1.97s | 2.27t, J=6.5 | 3.26m | 4.91m | 5.67bs |
| 7.33 | 0.88t, J=6.5 | 0.88t, J=6.5 | 1.20–1.80m, 22H(5+6) | 1.96s | 2.30t, J=6.5 | 3.23m | 4.82m | 5.76bs |
| 7.34 | 0.89t, J=6.5 | 0.89t, J=6.5 | 1.20–1.80m, 22H(5+5+1) | 1.97s | 2.29t, J=6.5 | 3.24m | 4.82m | 5.76bs |
| 7.35 | 0.89t, J=6.5 | 0.89t, J=6.5 | 1.20–1.80m, 22H(5+4+2) | 1.97s | 2.29t, J=6.5 | 3.23m | 4.88m | 5.75bs |
| 7.36 | 0.88t, J=6 | 1.20d, J=6 | 1.20–1.80m, 22H(5+3+3) | 1.97s | 2.30t, J=6.5 | 3.24m | 4.88m | 5.76bs |
| 7.37 | 0.89t, J=6 | 1.21d, J=6 | 1.20–1.80m, 24H(5+7) | 1.96s | 2.29t, J=6.5 | 3.24m | 4.82m | 5.76bs |
| | | | 26H(5+8) | | | | | |

*n is number of H;
figure in bracket is number of CH$_2$ groups

TABLE XXII

Elemental analysis of Carbamic acid salts based on the alkyl ω-aminoalkanoates

| Product No. | % C calc. | % C found | % H calc. | % H found | % N calc. | % N found |
|---|---|---|---|---|---|---|
| 1.1 | 63.26 | 63.19 | 10.62 | 10.69 | 5.90 | 5.82 |
| 1.2 | 64.51 | 64.59 | 10.83 | 10.75 | 5.57 | 5.62 |
| 1.3 | 65.62 | 65.47 | 11.01 | 11.18 | 5.28 | 5.45 |
| 1.4 | 66.63 | 66.59 | 11.18 | 11.42 | 5.01 | 4.98 |
| 1.5 | 67.54 | 67.58 | 11.33 | 11.35 | 4.77 | 4.80 |
| 1.6 | 68.36 | 68.34 | 11.47 | 11.60 | 4.56 | 4.73 |
| 1.7 | 69.11 | 69.14 | 11.60 | 11.48 | 4.36 | 4.40 |
| 1.8 | 70.44 | 70.41 | 11.82 | 11.78 | 4.01 | 3.98 |
| 1.9 | 71.57 | 71.69 | 12.01 | 11.78 | 4.01 | 3.98 |
| 1.10 | 63.26 | 63.29 | 10.62 | 10.60 | 5.90 | 5.95 |
| 1.11 | 64.51 | 64.50 | 10.3 | 10.85 | 5.57 | 5.55 |
| 1.12 | 65.62 | 65.43 | 11.01 | 11.05 | 5.28 | 5.26 |
| 1.13 | 66.63 | 66.61 | 11.18 | 11.17 | 5.01 | 5.04 |
| 1.14 | 67.54 | 67.71 | 11.33 | 11.35 | 4.77 | 4.76 |
| 1.15 | 68.36 | 68.39 | 11.47 | 11.45 | 4.56 | 4.58 |
| 1.16 | 69.11 | 69.29 | 11.60 | 11.89 | 4.36 | 4.48 |
| 1.17 | 69.81 | 69.64 | 11.72 | 11.49 | 4.17 | 4.30 |
| 1.18 | 71.03 | 71.00 | 11.92 | 11.89 | 3.85 | 3.83 |
| 1.19 | 72.07 | 72.26 | 12.10 | 12.07 | 3.58 | 3.81 |
| 1.20 | 64.51 | 64.39 | 10.83 | 10.84 | 5.57 | 5.80 |
| 1.21 | 65.62 | 65.65 | 11.01 | 11.03 | 5.28 | 5.25 |
| 1.22 | 66.63 | 66.82 | 11.18 | 11.21 | 5.01 | 5.23 |
| 1.23 | 67.54 | 67.55 | 11.33 | 11.30 | 4.77 | 4.79 |
| 1.24 | 68.36 | 68.59 | 11.47 | 11.45 | 4.56 | 4.34 |
| 1.25 | 69.11 | 69.24 | 11.60 | 11.39 | 4.36 | 4.38 |
| 1.26 | 69.81 | 60.78 | 11.72 | 11.73 | 4.17 | 4.15 |
| 1.27 | 70.44 | 70.42 | 11.82 | 11.85 | 4.01 | 3.88 |
| 1.28 | 71.58 | 71.60 | 12.01 | 11.99 | 3.71 | 3.70 |
| 1.29 | 72.54 | 72.53 | 12.17 | 12.34 | 3.45 | 3.47 |
| 1.30 | 69.11 | 69.13 | 11.60 | 11.57 | 4.36 | 4.39 |
| 1.31 | 69.81 | 69.70 | 11.72 | 11.49 | 4.17 | 4.19 |

TABLE XXIII

Elemental analysis of Carbamic acid salts based on the cycloalkyl ω aminoalkanoates

| Product No. | % C calc. | % C found | % H calc. | % H found | % N calc. | % N found |
|---|---|---|---|---|---|---|
| 4.1 | 69.55 | 69.48 | 11.04 | 10.93 | 4.38 | 4.22 |
| 4.2 | 69.12 | 68.91 | 7.86 | 7.95 | 5.20 | 5.37 |
| 4.3 | 68.96 | 68.91 | 9.74 | 9.35 | 4.87 | 5.01 |
| 4.4 | 70.44 | 70.56 | 10.91 | 11.15 | 4.21 | 4.36 |
| 4.5 | 69.94 | 69.70 | 8.18 | 8.38 | 4.94 | 5.05 |
| 4.6 | 69.73 | 69.56 | 9.70 | 9.49 | 4.65 | 4.82 |
| 4.7 | 71.05 | 70.85 | 11.05 | 11.32 | 4.04 | 3.89 |
| 4.8 | 70.68 | 70.95 | 8.47 | 8.22 | 4.71 | 4.63 |
| 4.9 | 74.44 | 74.23 | 9.91 | 10.12 | 4.44 | 4.64 |

TABLE XXV

Elemental analysis of Carbamic acid salts based on the ω-aminoalkyl alkanoates

| Product No. | % C calc. | % C found | % H calc. | % H found | % N calc. | % N found |
|---|---|---|---|---|---|---|
| 8.1 | 65.62 | 65.35 | 11.01 | 10.70 | 5.28 | 5.20 |
| 8.2 | 66.63 | 66.77 | 11.18 | 11.17 | 5.01 | 5.17 |
| 8.3 | 67.54 | 67.51 | 11.33 | 11.62 | 4.77 | 4.41 |
| 8.4 | 68.36 | 67.97 | 11.47 | 11.37 | 4.56 | 4.40 |
| 8.5 | 69.55 | 69.60 | 11.04 | 11.30 | 4.38 | 4.67 |
| 8.6 | 64.51 | 64.78 | 10.83 | 10.62 | 5.57 | 5.38 |
| 8.7 | 65.62 | 65.42 | 11.01 | 10.78 | 5.28 | 5.15 |
| 8.8 | 66.63 | 66.80 | 11.18 | 11.05 | 5.01 | 5.23 |
| 8.9 | 67.54 | 67.41 | 11.33 | 11.56 | 4.77 | 4.37 |
| 8.10 | 68.36 | 68.05 | 11.47 | 11.28 | 4.56 | 4.68 |

TABLE XXVI

The enhancement efficiency of selected Carbamic acid salts:

| Product No. | ER | Product No. | ER |
|---|---|---|---|
| 1.1 | 4.5 | 4.1 | 1.4 |
| 1.7 | 39.3 | 4.3 | 1.1 |
| 1.9 | 13.8 | 4.4 | 1.1 |
| 1.12 | 5.3 | 4.6 | 1.1 |
| 1.14 | 23.1 | 4.7 | 1.1 |
| 1.16 | 3.8 | 4.8 | 1.0 |
| 1.21 | 3.9 | 8.1 | 39.8 |
| 1.24 | 5.2 | 8.3 | 41.2 |
| 1.26 | 3.8 | 8.5 | 44.8 |
| 1.29 | 1.8 | 8.6 | 29.2 |
| 1.33 | 5.8 | 8.10 | 22.1 |

What is claimed is:

1. Carbamic acid salts of general formula (I)

$$X—CH_2—(CH_2)_n—COO—A—Y \quad (I)$$

wherein
either X is hydrogen and Y is a group of formula $NHCOO^-H_3N^+—A—OCO—(CH_2)_{n-1}—CH_3$, or X is a group of formula $NHCOO^-H_3N^+—(CH_2)_{n+1}—COO—A—H$ and Y is hydrogen, and wherein A is a $C_5$–$C_{16}$ alkylene or a $C_5$–$C_{12}$ cycloalkanediyl, benzocycloalkanediyl, bicycloalkanediyl or tricycloalkanediyl and n is an integer from 3 to 14.

2. A method for the preparation of carbamic acid salts of claim 1 wherein an amino acid hydrochloride of general formula $$Cl^-H_3N^+—(CH_2)_{n+1}—COOH$$

wherein n is as defined in claim 1, is reacted with thionyl chloride at a temperature of from 10° C. to 40° C. and the resulting aminoacylchloride hydrochloride is reacted with at least an equimolar amount of an alcohol selected from the group including primary monocyclic, bicyclic and tricyclic alcohols of general formula $$A—OH$$

wherein A is defined as in claim 1, in an aprotic medium at a temperature of from 20° C. to 90° C., giving rise to an amino acid ester hydrochloride which is then reacted with an amine in an aqueous or anhydrous medium, the basic ester being thereafter reacted with carbon dioxide.

3. A method for the preparation of carbamic acid salts of claim 1 wherein a carboxylic acid chloride of general formula $$CH_3—(CH_2)_n—COCl$$

wherein n is as defined in claim 1, is reacted with an α,ω-amino alcohol hydrochloride of general formula $$HO—A—NH_3^+Cl^-$$

wherein A is as defined in claim 1, at a temperature of from 20° C. to 90° C. in an aprotic medium, the amino ester hydrochloride being thereafter reacted with an amine in an aqueous or anhydrous medium and the basic amino ester being allowed to react with carbon dioxide.

4. Transdermal penetration enhancers destined for enhancing the penetration of physiologically active substances applied topically to human or animal skin in order to produce therapeutically effective concentrations of the active substances in deeper layers of the skin or produce therapeutically effective concentrations of the active substances in the circulatory system of living organisms, consisting of at least one compound of claim 1.

5. A method of enhancing the transdermal penetration of topical pharmaceutical and cosmetic preparations comprising:

placing the compounds of claim 1 in pharmaceutical and cosmetic preparations.

6. A method of enhancing the transdermal penetration of the hydrophobic vehicle of a topical preparation comprising:

placing the compounds of claim 1 in a hydrophobic vehicle of a topical preparation in the amount of from 0.1 to 5.0% w/w.

7. A method according to claim 9 wherein the compounds of claim 1 are placed in the topical preparation in the amount of from 0.5 to 2.5% w/w.

8. A method of enhancing the transdermal penetration of the hydrophilic medium of a topical preparation comprising:

placing the compounds of claim 1 in a hydrophilic medium of a topical preparation in the amount of 0.1 to 5.0% w/w.

9. A method according to claim 11 wherein the compounds of claim 1 are placed in the topical preparation in the amount of from 0.5 to 1% w/w.

* * * * *